(12) United States Patent
Badimon Maestro et al.

(10) Patent No.: US 11,486,884 B2
(45) Date of Patent: Nov. 1, 2022

(54) METHODS AND KITS FOR THE DIAGNOSIS AND RISK STRATIFICATION OF PATIENTS WITH ISCHEMIA

(71) Applicants: CONSEJO SUPERIOR DE INVESTIGACIONES CIENTÍFICAS, Madrid (ES); FUNDACIÓ INSTITUT DE RECERCA DE L'HOSPITAL DE LA SANTA CREU I SANT PAU, Barcelona (ES)

(72) Inventors: Lina Badimon Maestro, Barcelona (ES); Judit Cubedo Ràfols, Barcelona (ES); Teresa Padró Capmany, Barcelona (ES)

(73) Assignees: CONSEJO SUPERIOR DE INVESTIGACIONES CIENTÍFICAS, Madrid (ES); FUNDACIÓ INSTITUT DE RECERCA DE L'HOSPITAL DE LA SANTA CREU I SAINT PAU, Barcelona (ES)

( * ) Notice: Subject to any disclaimer, the term of this patent is extended or adjusted under 35 U.S.C. 154(b) by 0 days.

(21) Appl. No.: 16/092,703

(22) PCT Filed: Apr. 12, 2017

(86) PCT No.: PCT/EP2017/058768
§ 371 (c)(1),
(2) Date: Oct. 10, 2018

(87) PCT Pub. No.: WO2017/178521
PCT Pub. Date: Oct. 19, 2017

(65) Prior Publication Data
US 2019/0128900 A1 May 2, 2019

(30) Foreign Application Priority Data
Apr. 12, 2016 (EP) .................................. 16382167

(51) Int. Cl.
*G01N 33/68* (2006.01)
(52) U.S. Cl.
CPC ... *G01N 33/6893* (2013.01); *G01N 2333/775* (2013.01); *G01N 2400/00* (2013.01); *G01N 2440/38* (2013.01); *G01N 2800/2871* (2013.01); *G01N 2800/324* (2013.01); *G01N 2800/50* (2013.01); *G01N 2800/52* (2013.01)
(58) Field of Classification Search
CPC .......... G01N 33/6893; G01N 2400/00; G01N 2440/38; G01N 2800/50; G01N 2800/52; G01N 2333/775; G01N 2800/2871; G01N 2800/324; G01N 2800/56
See application file for complete search history.

(56) References Cited

U.S. PATENT DOCUMENTS

| 6,140,045 A | 10/2000 | Wohlstadter et al. |
| 6,197,599 B1 | 3/2001 | Chin et al. |
| 2009/0166224 A1* | 7/2009 | Yang ........................ C07K 1/22 205/792 |
| 2012/0190576 A1* | 7/2012 | Narimatsu ............... C07K 9/00 506/9 |
| 2013/0123137 A1 | 5/2013 | Reichardt et al. |
| 2018/0142009 A1 | 5/2018 | Quinn et al. |

FOREIGN PATENT DOCUMENTS

| CN | 108093648 A | 5/2018 |
| JP | 2012107932 A | 6/2012 |
| WO | 9904260 A1 | 1/1999 |
| WO | 2011098645 A1 | 8/2011 |

OTHER PUBLICATIONS

Cancer Epidemiol Biomarkers Prev. Jun. 2011; 20(6): 1222-1229. (Year: 2011).*
Cubedo et al., "Proteomic Signature of Apolipoprotein J in the Early Phase of New-Onset Myocardial Infarction", Journal of Proteome Research, 2011,, pp. 211-220, vol. 10, No. 1.
Cubedo et al., "Glycoproteome of Human Apolipoprotein A-I: N- and O-Glycosylated Forms are Increased in Patients with Acute Myocardial Infarction", Transational Research, 2014, pp. 209-222, vol. 164, No. 3.
Kapron et al., "Identification and Characterization of Glycosylation Sites in Human Serum Clusterin", Protein Science, 1997, pp. 2120-2133, vol. 6.
Legendre, "Immobilon-P Transfer Membrane: Applications and Utility in Protein Biochemical Analysis", Biotechniques, 1990, pp. 788-805, vol. 9, No. 6.
Oguri, "Analysis of Sugar Chain-Binding Specificity of Tomato Lectin Using Lectin Blot: Recognition of High Mannose-Type N-Glycans Produced by Plants and Yeast", Glycoconjugate Journal, 2005, pp. 453-461, vol. 22.
Shalon et al., "A Dna Microarray System for Analyzing Complex DNA Samples Using Two-Color Fluorescent Probe Hybridization", Genome Research, 1996, pp. 639-645.
Wu et al., "Studies on the Binding of Wheat Germ Agglutinin (*Triticum vulgaris*) to O-Glycans", FEBS Letters, Dec. 4, 1998, pp. 315-319, vol. 440, No. 3.
Dhingra et al., "Biomarkers in Cardiovascular Disease: Statistical Assessment and Section on Key Novel Heart Failure Biomarkers", Trends Cardiovascular Med, 2017, pp. 123-133, vol. 27, No. 2.

(Continued)

*Primary Examiner* — Tracy Vivlemore
*Assistant Examiner* — Nam P Nguyen
(74) *Attorney, Agent, or Firm* — Thompson Coburn LLP; William A. Holtz

(57) ABSTRACT

The invention relates to methods for the diagnosis of ischemia or ischemic tissue damage, methods for predicting the progression of ischemia in a patient having suffered an ischemic event, for determining the prognosis of a patient having suffered an ischemic event and for determining the risk that a patient suffering from stable coronary disease suffers a recurrent ischemic event based on the detection of the levels of glycosylated Apo J. The invention relates as well to a method for the determination of glycosylated Apo J in a sample.

28 Claims, 15 Drawing Sheets

(56) References Cited

OTHER PUBLICATIONS

Charlwood et al., "Use of Proteomic Methodology for the Characterization of Human Milk Fat Globular Membrane Proteins", Analytical Biochemistry, 2002, pp. 314-324, vol. 301.
Gbormittah et al., "Clusterin Glycopeptide Variant Characterization Reveals Significant Site-Specific Glycan Changes in the Plasma of Clear Cell Renal Cell Carcinoma", Journal of Proteome Research, 2015, pp. 2425-2436, vol. 14.
Matsuda et al., "Lectin Microarray-Based Sero-Biomarker Verification Targeting Aberrant O-Linked Glycosylation on Mucin 1", Analytical Chemistry, 2015, pp. 7274-7281, vol. 87.
Bartl et al., "Multiple Receptors Mediate aproJ-Dependent Clearance of Cellular Debris into Nonprofessional Phagocytes", Experimental Cell Research, 2001, pp. 130-141, vol. 271.
Fanayan et al., "Using Lectins to Harvest the Plasma/Serum Glycoproteome" Electrophoresis, 2012, pp. 1746-1754, vol. 33.
Naeem et al., "Glycoprotein Targeting and Other Applications of Lectins in Biotechnology", Current Protein and Peptide Science, 2007, pp. 261-271, vol. 8.
Ohtsubo et al., "Glycosylation in Cellular Mechanisms of Health and Disease", Cell, Sep. 8, 2006, pp. 855-867.

\* cited by examiner

METHODS AND KITS FOR THE DIAGNOSIS AND RISK STRATIFICATION OF PATIENTS WITH ISCHEMIA

CROSS-REFERENCE TO RELATED APPLICATIONS

This patent application is a national phase application of PCT/EP2017/058768, filed on Apr. 12, 2017, claiming the benefit of European Patent Application No. 16382167.1, filed on Apr. 12, 2016, both of which are incorporated herein by reference in their entireties.

FIELD OF THE INVENTION

The present invention relates to biomarkers for the prognosis, diagnosis and risk stratification of individuals with myocardial or cerebral ischemia or tissue ischemic damage associated thereto, as well as for the presentation of recurrent ischemic events in individuals with stable coronary artery disease (CAD).

BACKGROUND OF THE INVENTION

Acute coronary syndromes (ACS) and cerebrovascular events are the most frequent clinical manifestations of atherothrombosis, and represent a major cause of death and disability worldwide. Early diagnosis is essential due to the importance of early revascularization and the high risk of death and/or loss of quality of life. Is in this context that biomarkers arise as important tools to complement clinical assessment for the diagnosis, triage, risk stratification, and management of patients with suspected ACS and to differentiate ischemic vs. haemorrhagic stroke. These biomarkers should be informative of the pathological process and represent an alternative for more complex and costly diagnostic techniques (as magnetic resonance, among others).

Indeed, there are a high percentage of admissions at the emergency room due to non-cardiac problems that curse with similar symptoms than those of cardiac ischemic events (pain due to respiratory or muscular pathologies). In the case of cerebrovascular disease there is an urgent need of having discriminators of hemorrhagic vs. ischemic stroke so that patient management can be accordingly and rapidly initiated.

Therefore, there is an unmet need for the identification of new biomarkers for the early, specific and sensitive detection of ischemia. Until now, markers of inflammation, cardiac function, and necrosis have been studied. However, it is not clear whether their measurement would be useful in the diagnosis and prognosis of ischemic syndromes. Ischemic organ damage usually precedes tissue necrosis and if timely detected could be reversed. This lack of existing markers for the accurate and early detection of ischemia incurs in elevated unnecessary economic costs worldwide.

Nowadays, the diagnosis and management of acute coronary syndromes (ACS) are based on clinical assessment, electrocardiogram findings and troponin levels (the only group of accepted biomarkers). The application of this protocol entails several limitations that make indispensable the search of new biomarkers for the management of patients with myocardial ischemia. The first disadvantage is that cardiac troponins (cTn) are markers of irreversible necrosis (cellular death), an advanced stage of myocardial lesion. Furthermore, high-sensitivity cTn assays (hs-cTn) have revealed a certain unspecificity. In addition, current guidelines highlight the need of performing serial hs-cTn measurements to make an adequate triage of patients with acute chest pain.

A method for detecting ischemic tissue damage based in a shift in the isoforms' distribution profile of apolipoprotein J (Apo J) has been described in the publication WO2011098645 as well as in Cubedo, J., et al., (J. Proteome Res., 2011, 10: 211-220). In those studies, two different groups of Apo J isoforms, Apo J-15 and Apo J-29, were identified by bidimensional electrophoresis followed by mass spectrometry. These Apo J forms were associated with tissue injury and, specifically, with cardiac damage due to an AMI. In ischemic damage timely and accurate detection of the ischemic event is crucial in order to prevent its progression that could lead to the irreversible injury of the tissue. In this scenario, the methodology based in bi-dimensional electrophoresis followed by mass spectrometry for the determination of the changes in Apo J distribution profile could not be used in the clinical practice as they are too complex, lengthy and expensive to be used in diagnosis of ischemia.

Accordingly, there is a need in the art for improved methods for the detection of vascular damage and AMI in particular.

SUMMARY OF THE INVENTION

In a first aspect, the invention relates to a method for the diagnosis of ischemia or ischemic tissue damage in a subject comprising determining in a sample of said subject the levels of glycosylated Apo J containing N-acetylglucosamine (GlcNAc) residues or the levels of glycosylated Apo J containing N-acetylglucosamine (GlcNAc) and sialic acid residues or to a method for the diagnosis of ischemia or ischemic tissue damage in a subject comprising determining in a sample of said subject the levels of glycosylated Apo J which is capable of specifically binding to the *Datura stramonium* lectin or the levels of glycosylated Apo J which is capable of specifically binding to the *Triticum vulgaris* lectin.

In a second aspect, the invention relates to a method for predicting the progression of ischemia in a patient having suffered an ischemic event or for determining the prognosis of a patient having suffered an ischemic event, comprising determining in a sample of said patient the levels of glycosylated Apo J, wherein decreased levels of glycosylated Apo J with respect to a reference value are indicative that the ischemia is progressing or of a poor prognosis of the patient.

In another aspect, the invention relates to a method for determining the risk that a patient suffering from stable coronary disease suffers a recurrent ischemic event comprising determining in a sample of said patient the levels of glycosylated Apo J, wherein decreased levels of glycosylated Apo J with respect to a reference value are indicative that the patient shows an increased risk of suffering a recurrent ischemic event.

In another aspect, the invention relates to a kit comprising
a. A first reagent which is a lectin which specifically binds to a glycan residue selected from N-acetylglucosamine and sialic acid and
b. A second reagent which is capable of specifically binding to the Apo J polypeptide.

In another aspect, the invention relates to a kit according to the invention for the diagnosis of ischemia or ischemic tissue damage in a patient, for determining the progression of ischemia in a patient having suffered an ischemic event, for the prognosis of a patient having suffered an ischemic event or for determining the risk that a patient suffering from stable coronary disease suffers a recurrent ischemic event.

In yet another aspect, the invention relates to a method for the determination of glycosylated Apo J in a sample comprising the steps of:
(i) Contacting the sample with a lectin which specifically binds to a glycan residue present in glycosylated Apo J under conditions adequate for the formation of a complex between the glycosylated Apo J in the sample and the lectin and
(ii) Detecting the amount of complex containing the lectin and the glycosylated Apo J

Representative pattern of Apo J cluster in 2-DE gels from control and ischemia pre-AMI serum samples. Apo J in serum was detected as a cluster of 13 spots with a pI range between 4.5 and 5.0 and a molecular mass between 37.1 and 47.3 kDa. Spots identified as Apo J were numbered from acidic to basic pH. Spot 2 was only apparent in ischemia pre-AMI-patients. Note that spots marked as 1, 3, 7, 8, 10, 11, and 13 depicted enhanced detection levels in ischemia pre-AMI, whereas spots 6 and 9 depicted a reduced intensity in ischemia pre-AMI gels compared to the control group. Spots 3, 7, 8 and 11 are Apo J-29, and spots 6 and 9 are Apo J-15.

Figure 2:
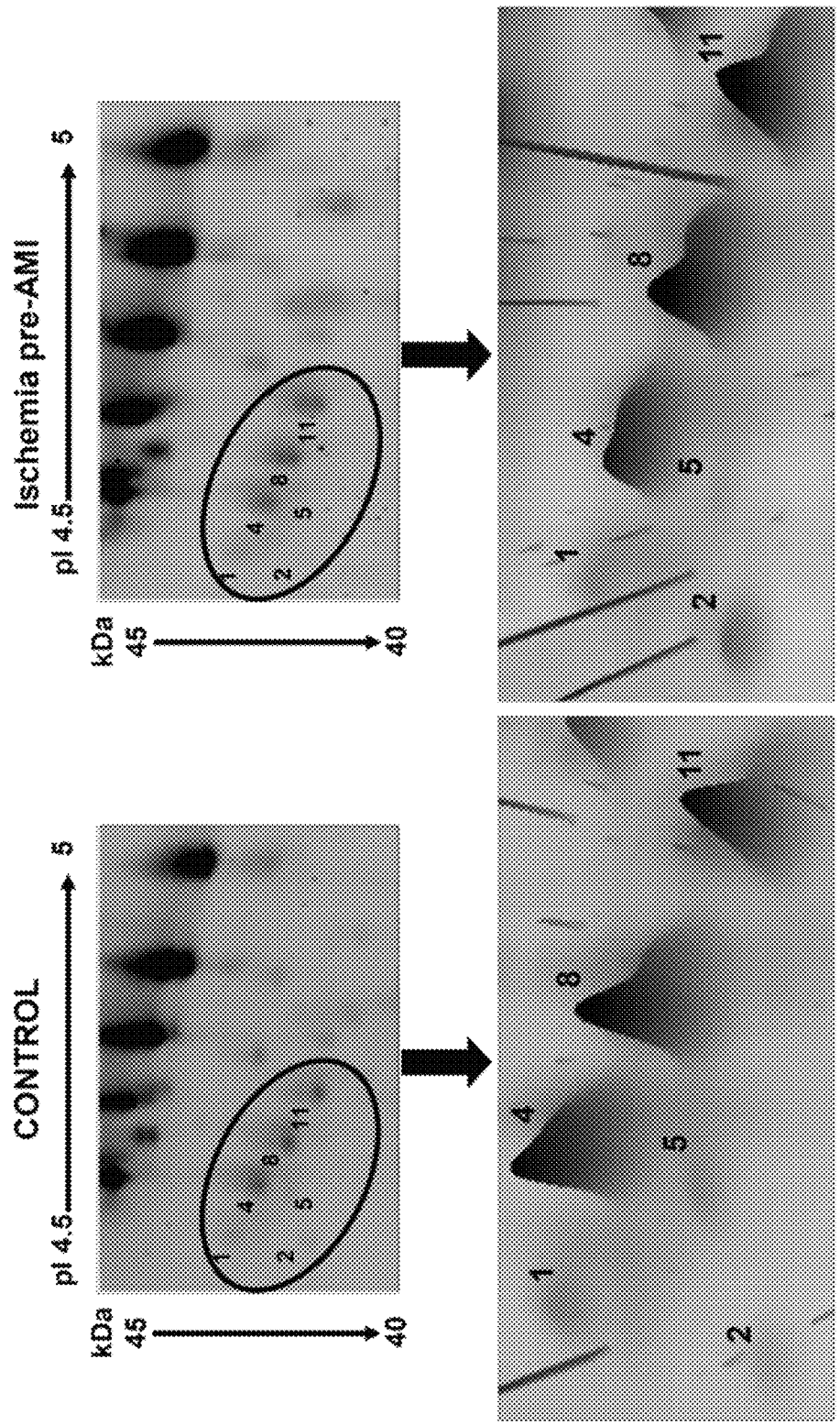

FIG. 2. Glycosylated Apo J Forms.

Representative 2-DE images of the Apo J cluster in the glycosylated serum fraction (isolated through its binding to a mixture of Concanavalin A and *Triticum vulgaris* lectins) from (A) healthy donors and (B) ischemia pre-AMI-patients. Six spots (1, 2, 4, 5, 8, and 11) corresponding in pI and MW with those of total serum were detected. As for FIG. 1, spots were numbered from acidic to basic pH. Intensity of Apo J spots was lower in ischemia pre-AMI-patients than in controls. The decrease was more evident in spots 4 and 8.

Figure 3:
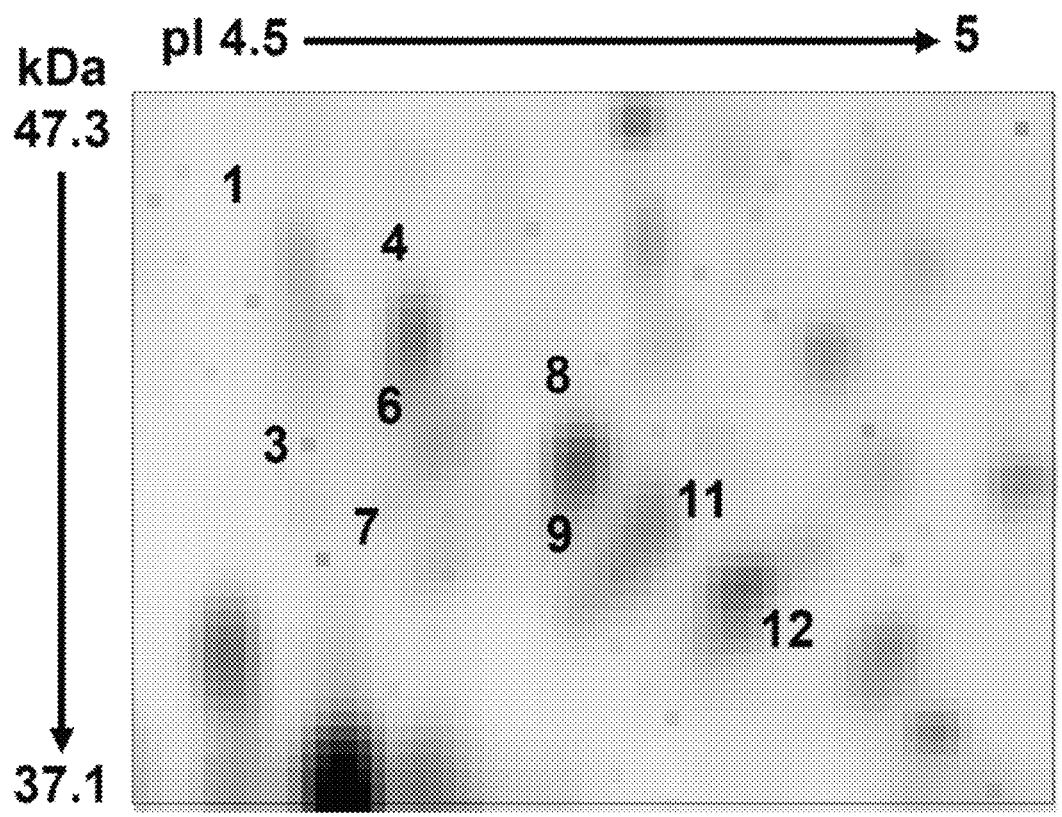

FIG. 3. O-Glycosylated Apo J Forms.

Representative 2-DE image of the Apo J cluster in the O-glycosylated serum fraction (isolated through its binding to *Artocarpus integrifolia* lectin). Nine spots were detected (1, 3, 4, 6, 7, 8, 9, 11 and 12) corresponding in pI and MW with those of total serum. As for FIGS. 1 and 2, spots were numbered from acidic to basic pH.

Figure 4:
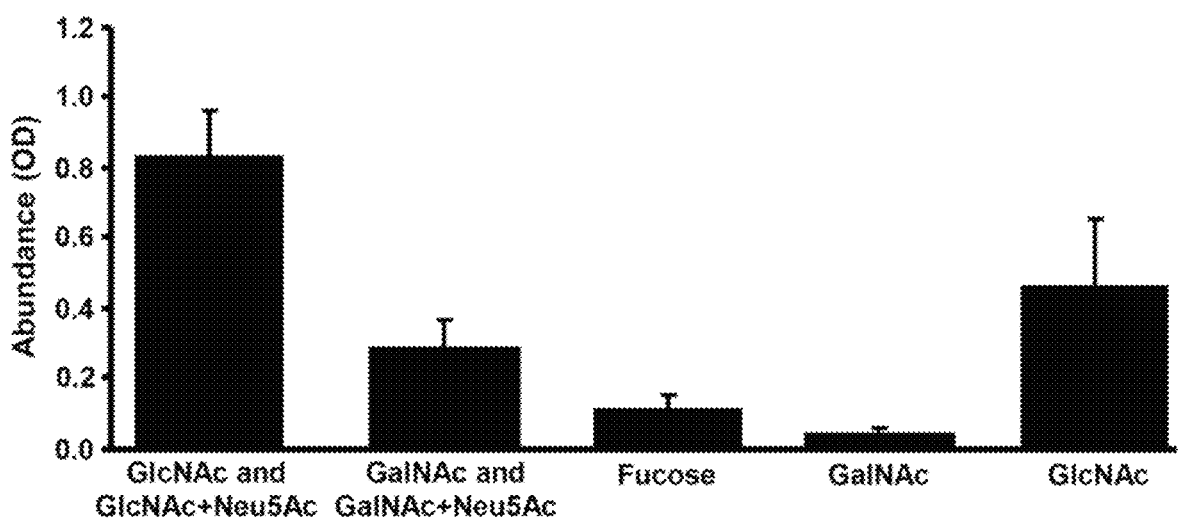

FIG. 4. Abundance of Apo J Glycosylated Forms.

Bar diagram showing the abundance of the different Apo J glycosylated forms in human plasma samples by the specific measurement with a novel and original immunoaffinity enzymatic-glycosylation assay or EGA.

Figure 5:
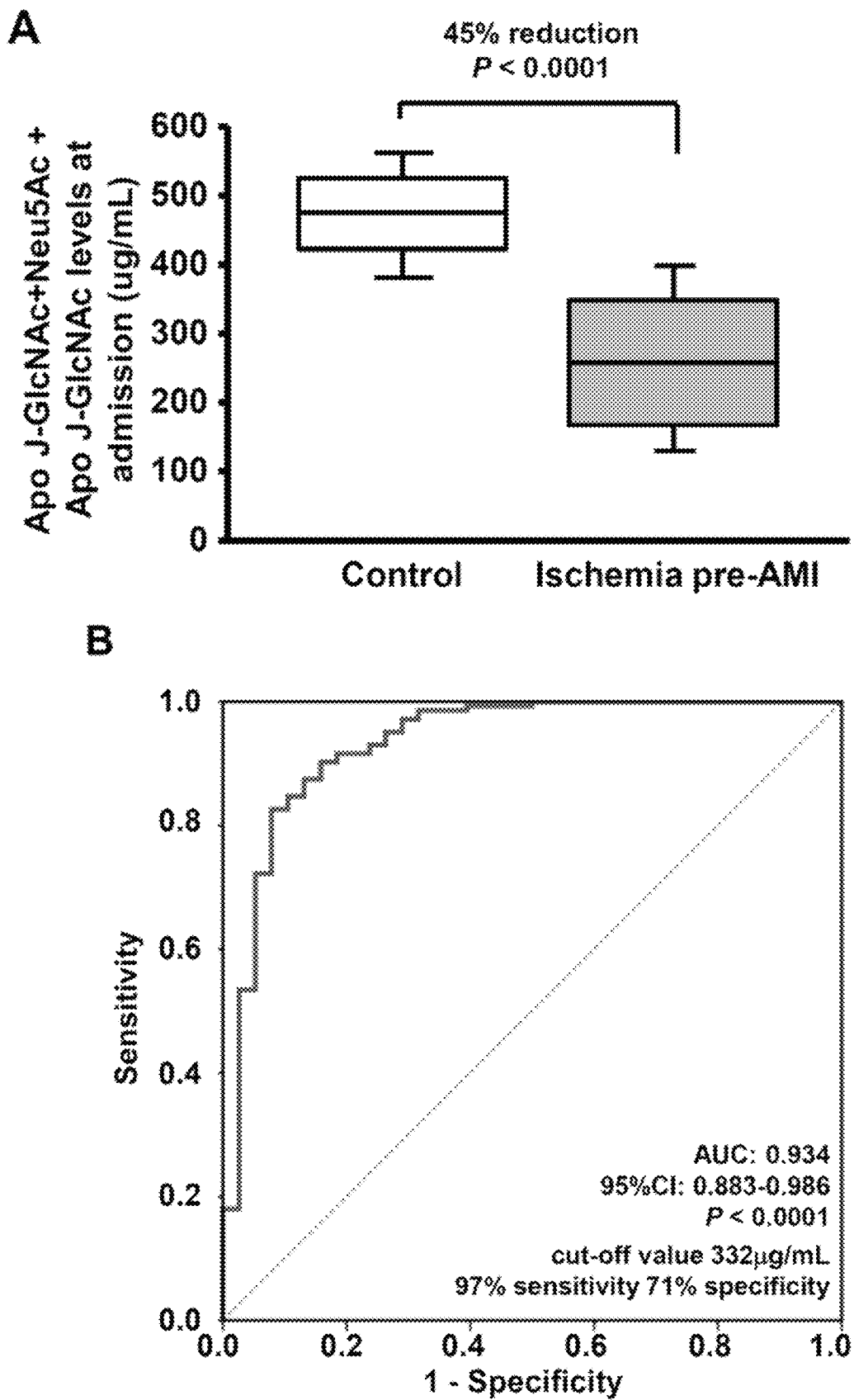

FIG. 5. Diagnostic Value.

(A) Box-plot showing Apo J-GlcNAc+Neu5Ac+Apo J-GlcNAc levels in the early phase of ischemia (N=38) and in healthy subjects (N=144). (B) Receiver operating curve (ROC) showing the diagnostic value for the presence of myocardial ischemia of Apo J-GlcNAc+Neu5Ac+Apo J-GlcNAc levels with an area under the curve (AUC) of 0.934 (P<0.0001) and a cut-off value of 332 µg/mL with 97% of sensitivity and 71% of specificity.

Figure 6:
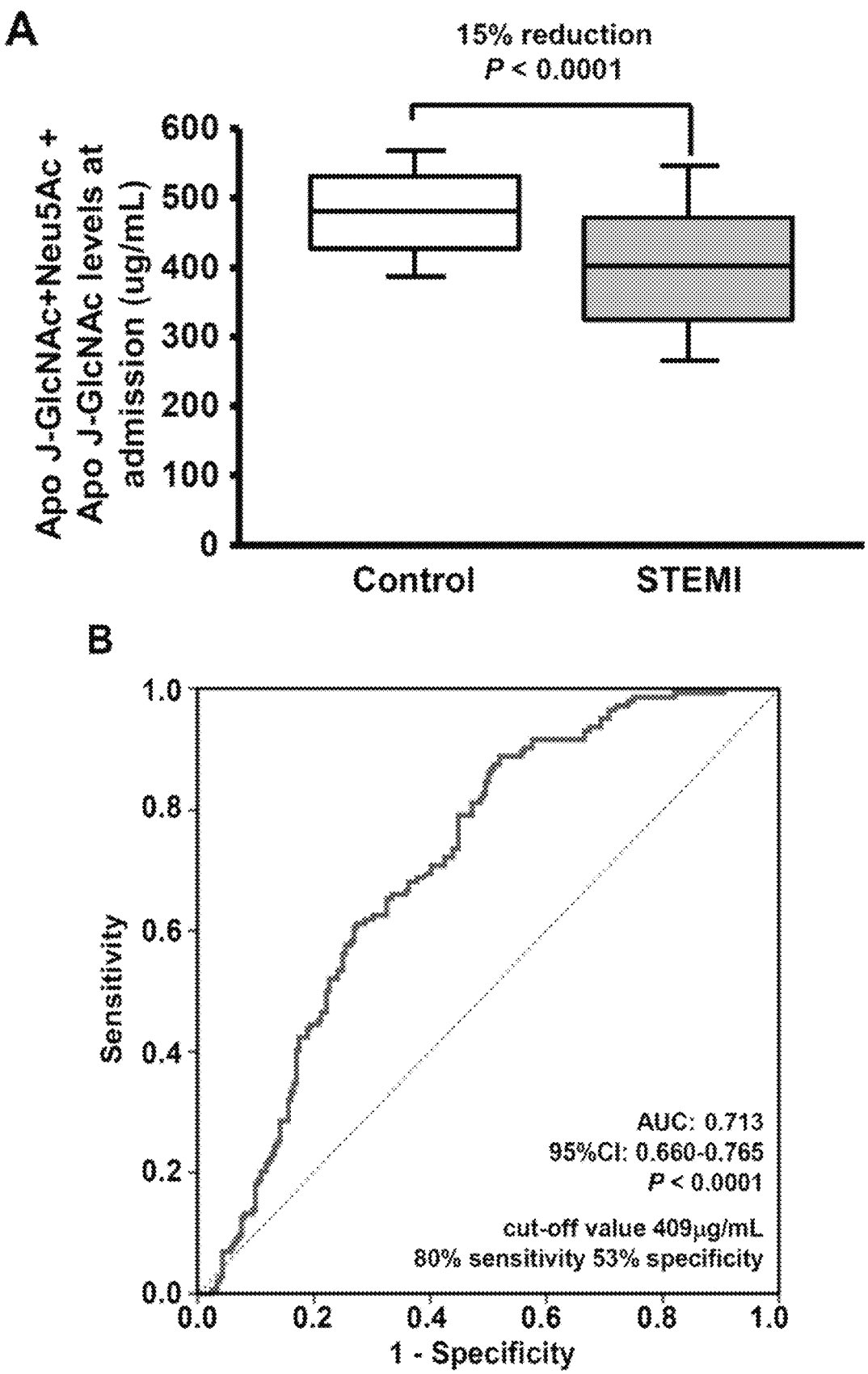
Figure 6:
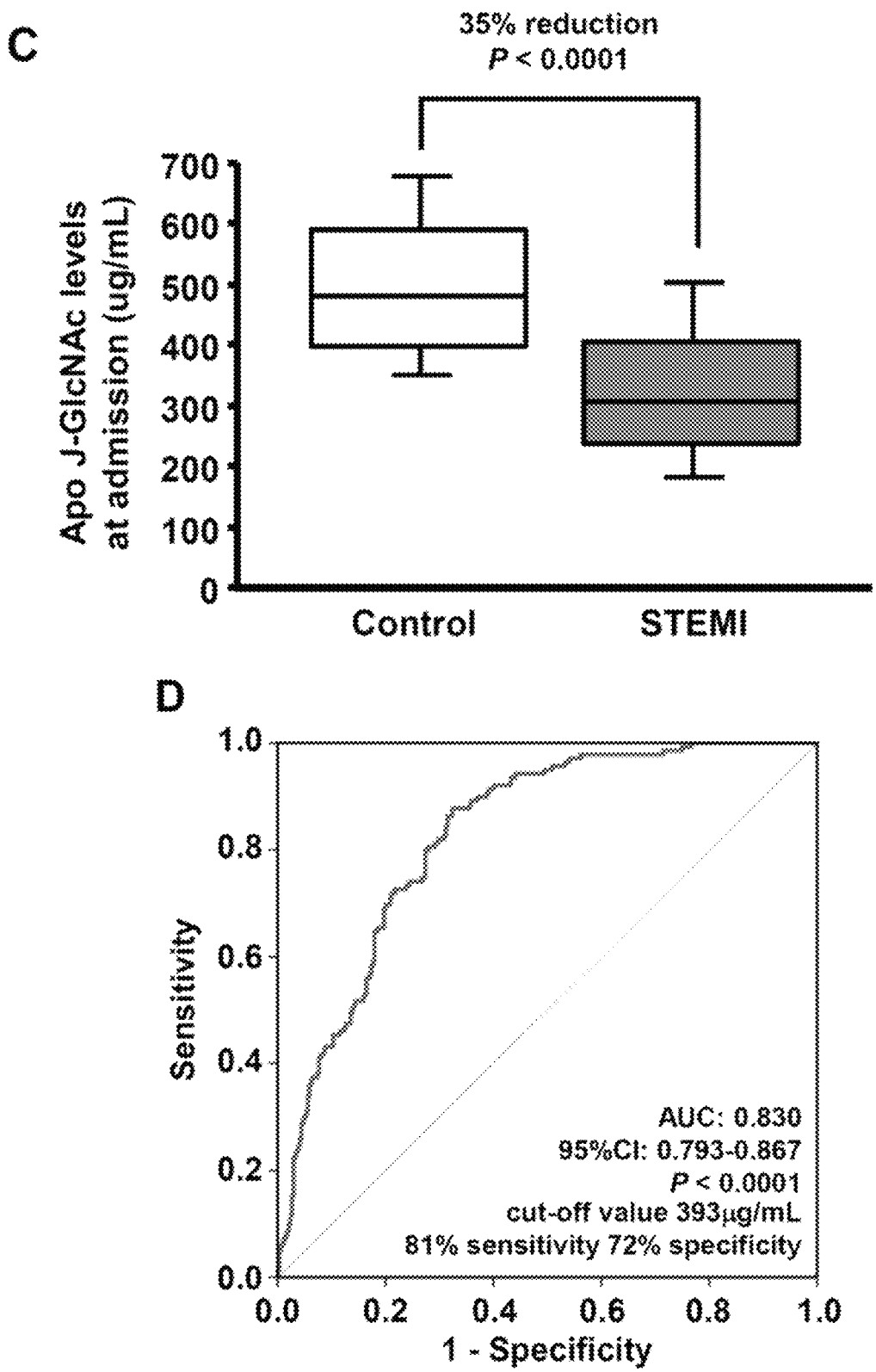

FIG. 6. Diagnostic Value in STEMI-Patients.

(A) Box-plot showing Apo J-GlcNAc+Neu5Ac+Apo J-GlcNAc levels in STEMI-patients at the moment of admission (N=212) and in healthy subjects (N=144). (B) Receiver operating curve (ROC) showing the discriminating value for the presence of ischemia of Apo J-GlcNAc+Neu5Ac+Apo J-GlcNAc levels with an area under the curve (AUC) of 0.713 (P<0.0001) and a cut-off value of 409 µg/mL with 80% of sensitivity and 53% of specificity. (C) Box-plot showing Apo J-GlcNAc levels in STEMI-patients at the moment of admission (N=340) and in healthy subjects (N=139). (B) Receiver operating curve (ROC) showing the discriminating value for the presence of ischemia of Apo J-GlcNAc levels with an area under the curve (AUC) of 0.830 (P<0.0001) and a cut-off value of 393 µg/mL with 81% of sensitivity and 72% of specificity.

Figure 7:
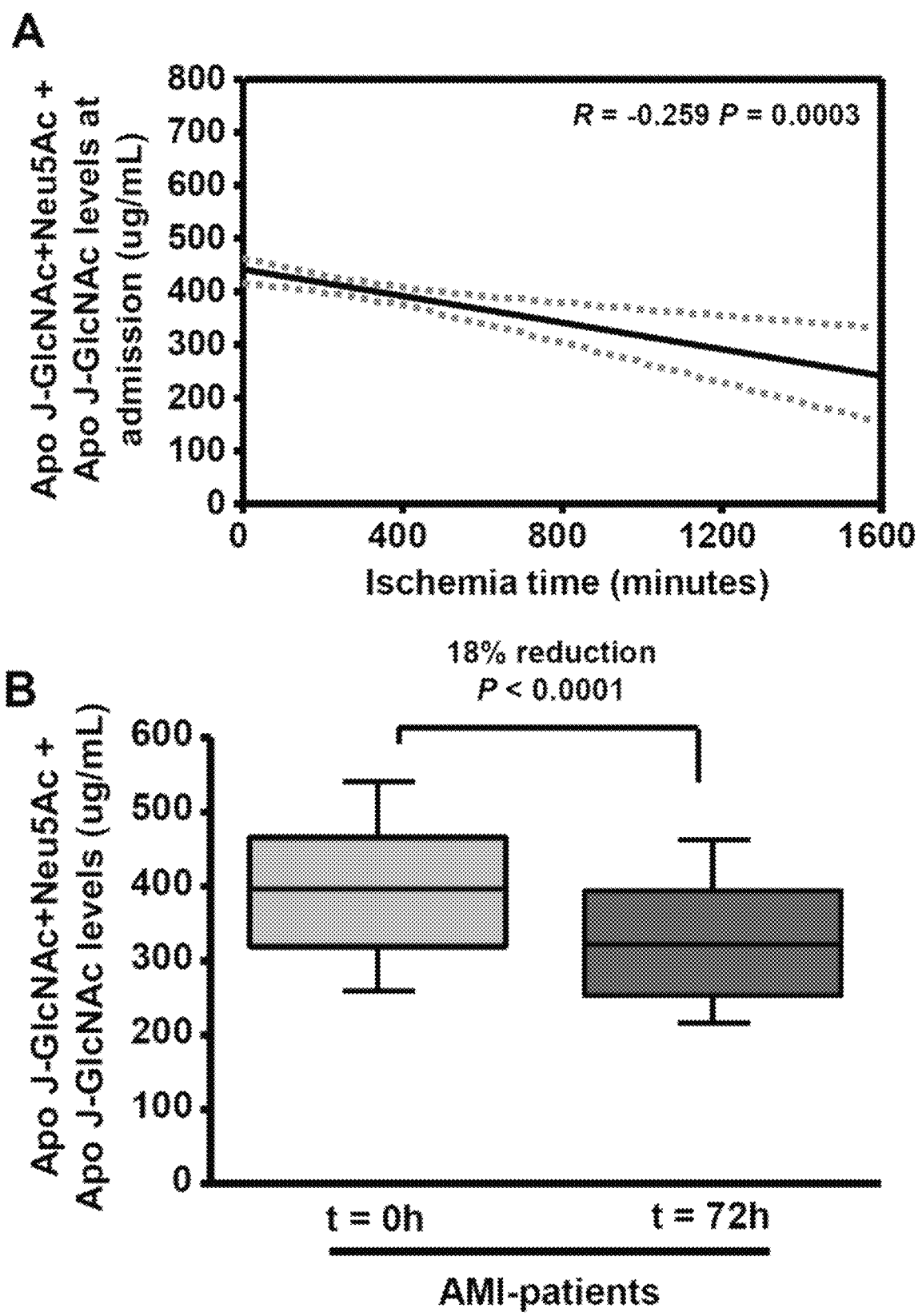
Figure 7:
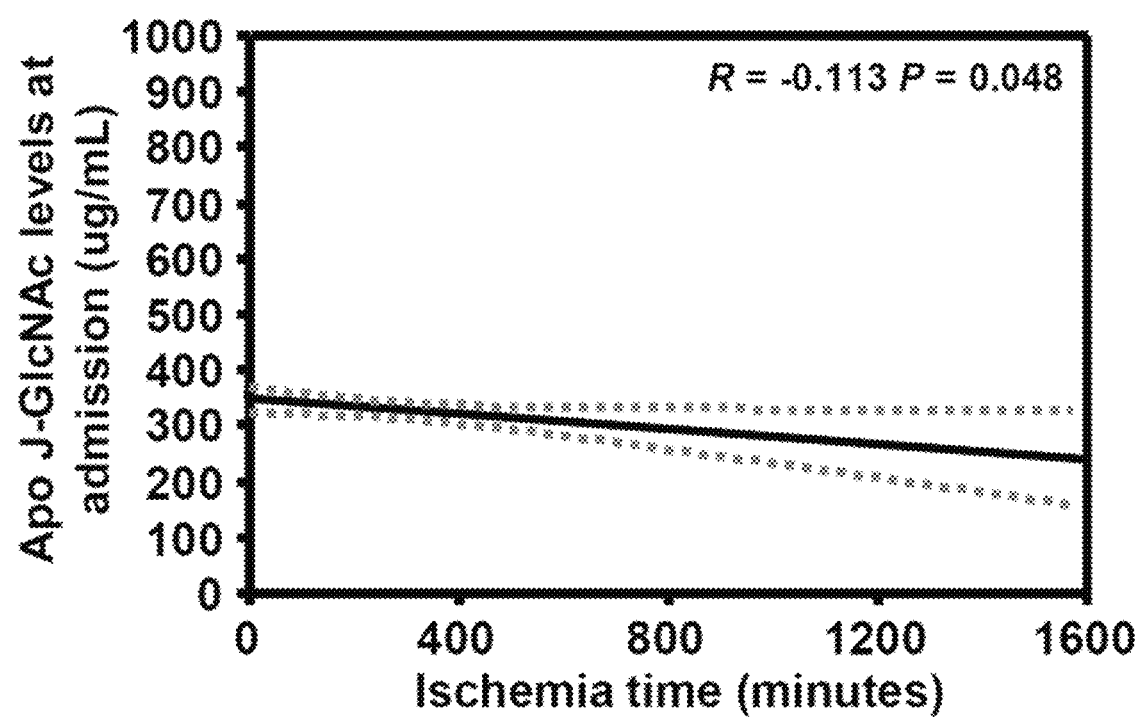

FIG. 7. Ischemia Progression.

(A) Regression plot showing the inverse and significant correlation between Apo J-GlcNAc+Neu5Ac+Apo J-GlcNAc levels at admission and ischemia time. (B) Box-plot showing the progressive decrease in Apo J-GlcNAc+Neu5Ac+Apo J-GlcNAc levels in 82 STEMI-patients 3 days after admission (t=72 h). (C) Regression plot showing the inverse and significant correlation between Apo J-GlcNAc levels at admission and ischemia time.

Figure 8:
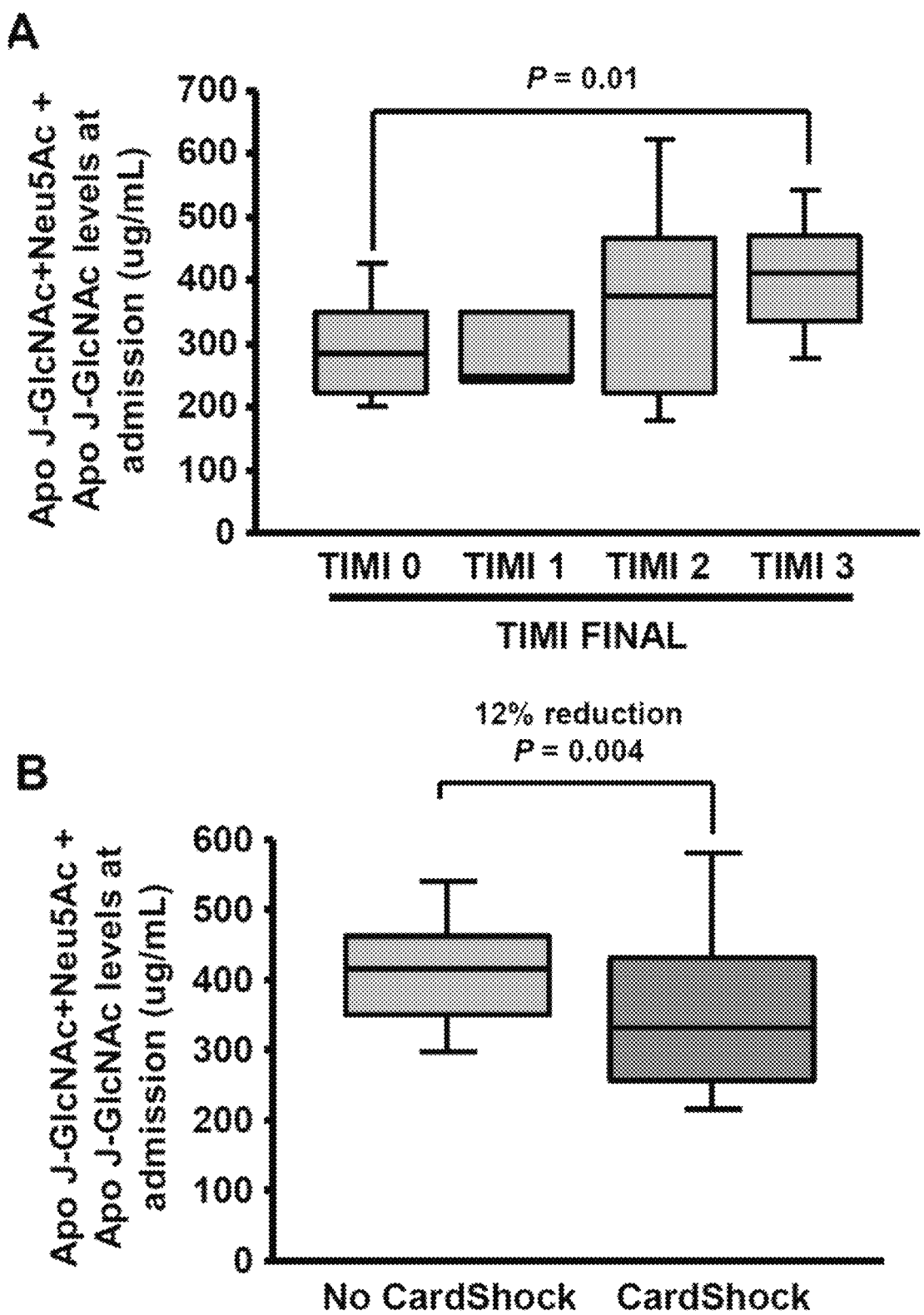

FIG. 8. Prognostic Value.

Box-plots showing the significant differences in Apo J-GlcNAc+Neu5Ac+Apo J-GlcNAc levels at admission in relation to (A) the final TIMI flow grade, which is known to be directly related to in-hospital and 6-months mortality; and (B) the presence of cardiogenic shock (65 patients with cardiogenic shock and 147 without) which is associated with a poorer prognosis after suffering a STEMI.

Figure 9:
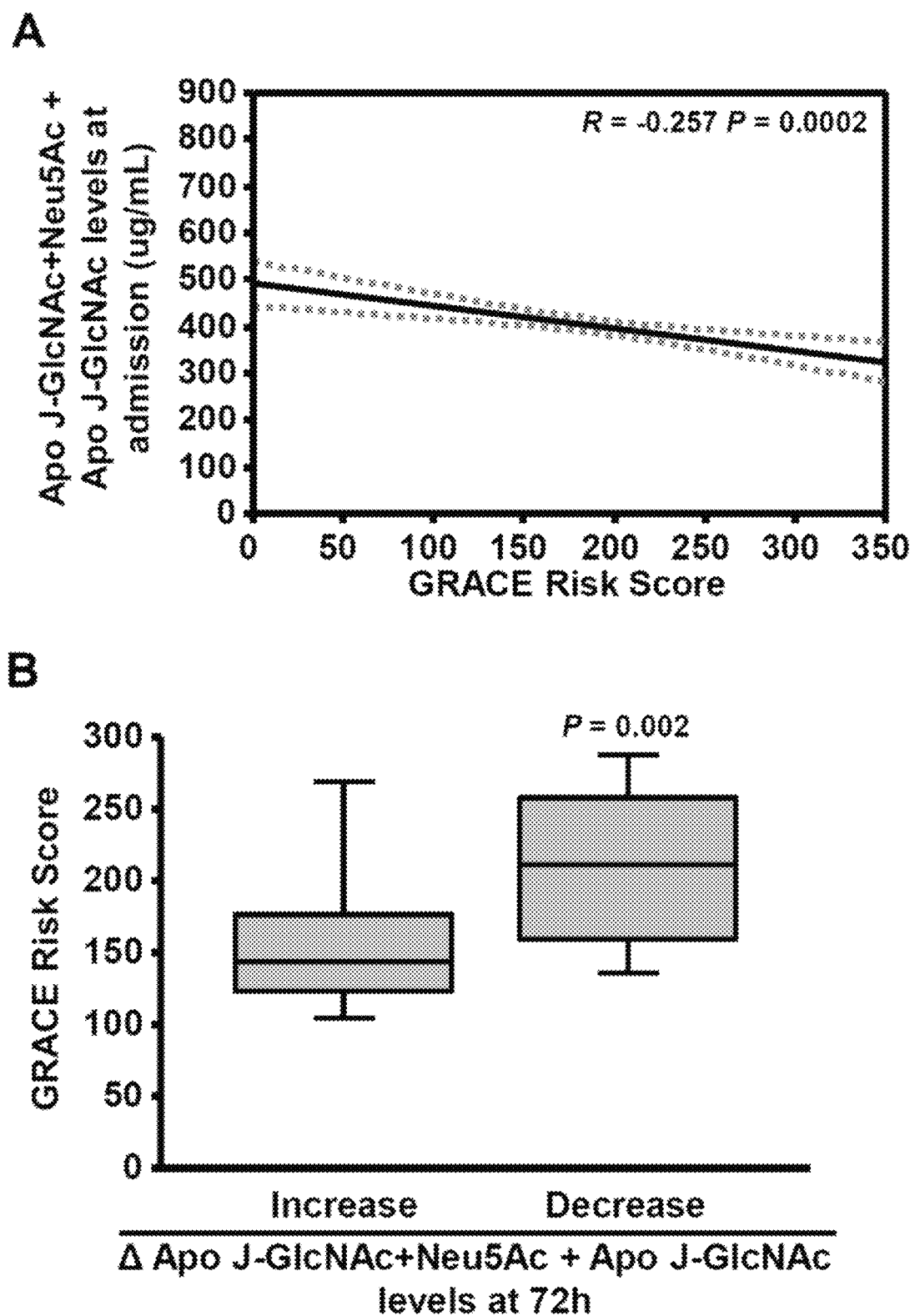
Figure 9:
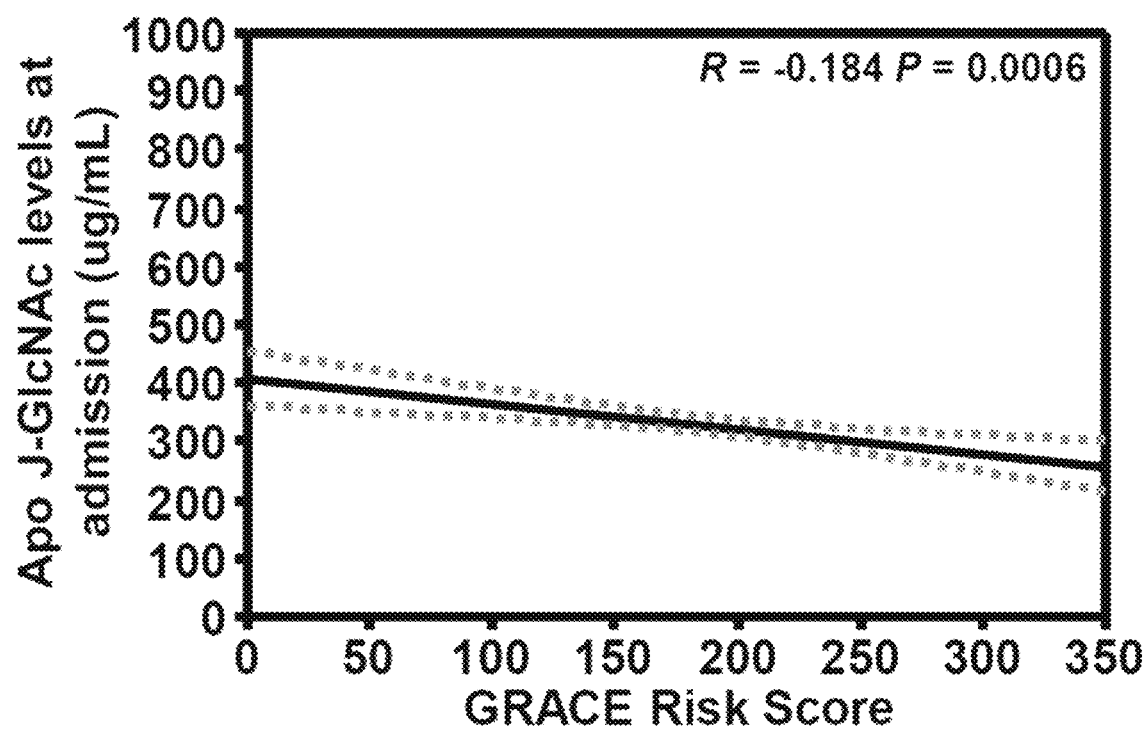

FIG. 9. Risk Stratification.

(A) Regression plot showing the inverse and significant correlation between Apo J-GlcNAc+Neu5Ac+Apo J-GlcNAc levels at admission and the GRACE Risk Score. (B) Box-plot showing the association between highest GRACE Risk Score values and the decrease in Apo J-GlcNAc+Neu5Ac+Apo J-GlcNAc levels 3 days after admission in STEMI-patients. (C) Regression plot showing the inverse and significant correlation between Apo J-GlcNAc levels at admission and the GRACE Risk Score.

Figure 10:
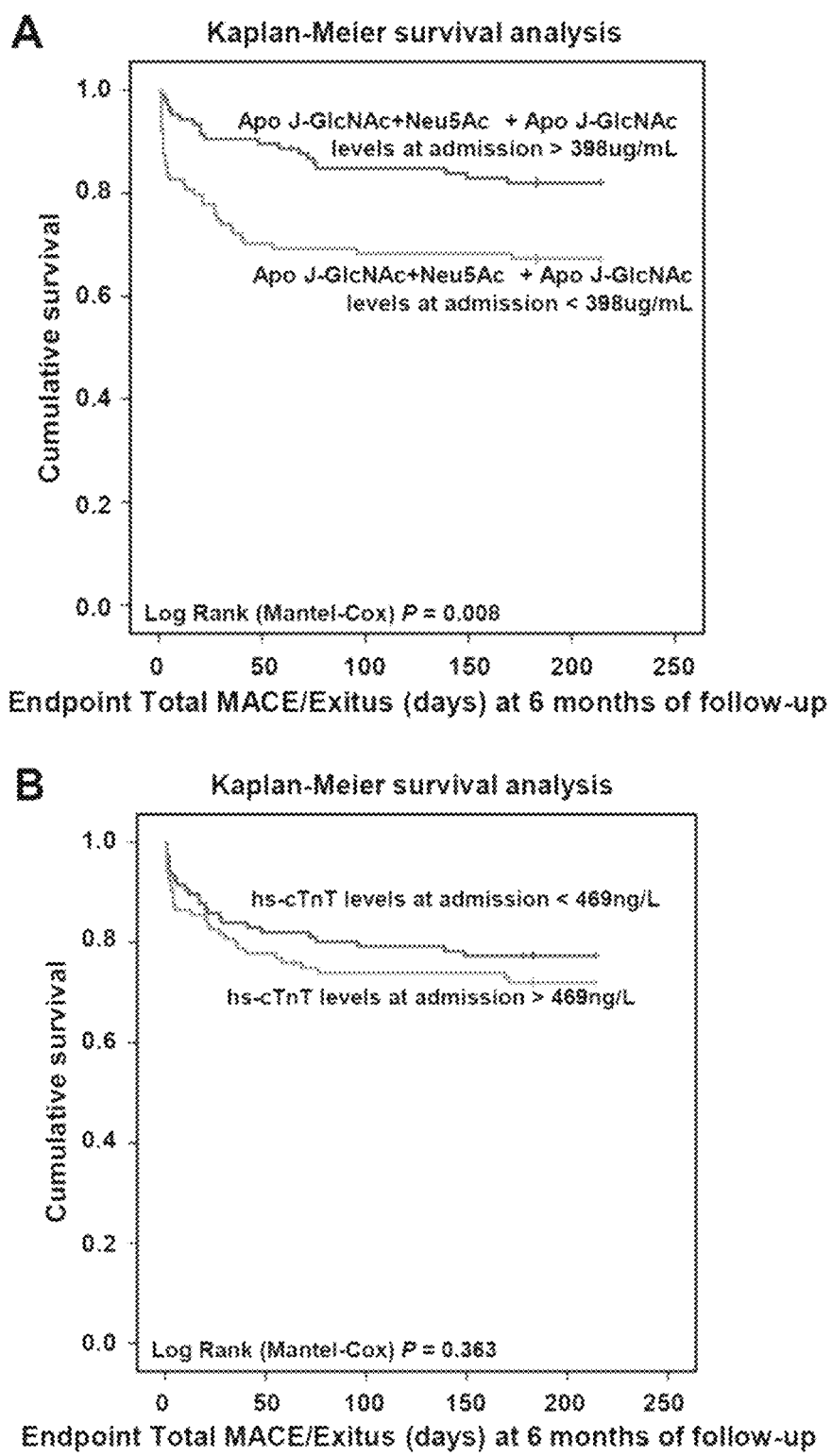
Figure 10:
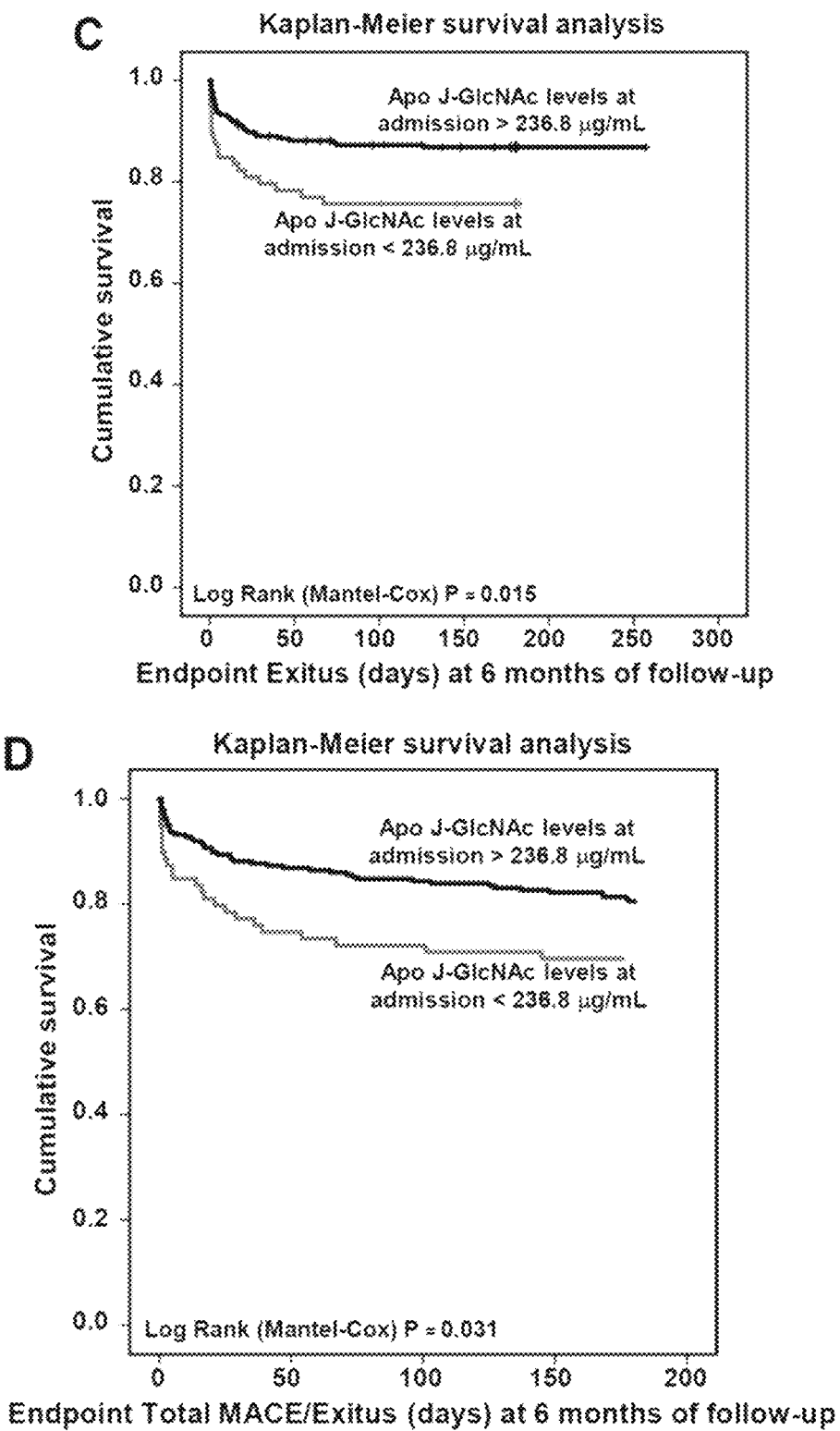

FIG. 10. Recurrent Events and Mortality at 6-Months Follow-Up in STEMI Patients.

Kaplan-Meier curves showing the impact of: Apo J-GlcNAc+Neu5Ac+Apo J-GlcNAc (A) and T troponin (B) levels at admission the presence of a recurrent ischemic event or death after 6 months of follow-up; and Apo J-GlcNAc levels at admission and mortality (C) or the combination of a recurrent ischemic event and death (D) after 6 months of follow-up.

Figure 11:
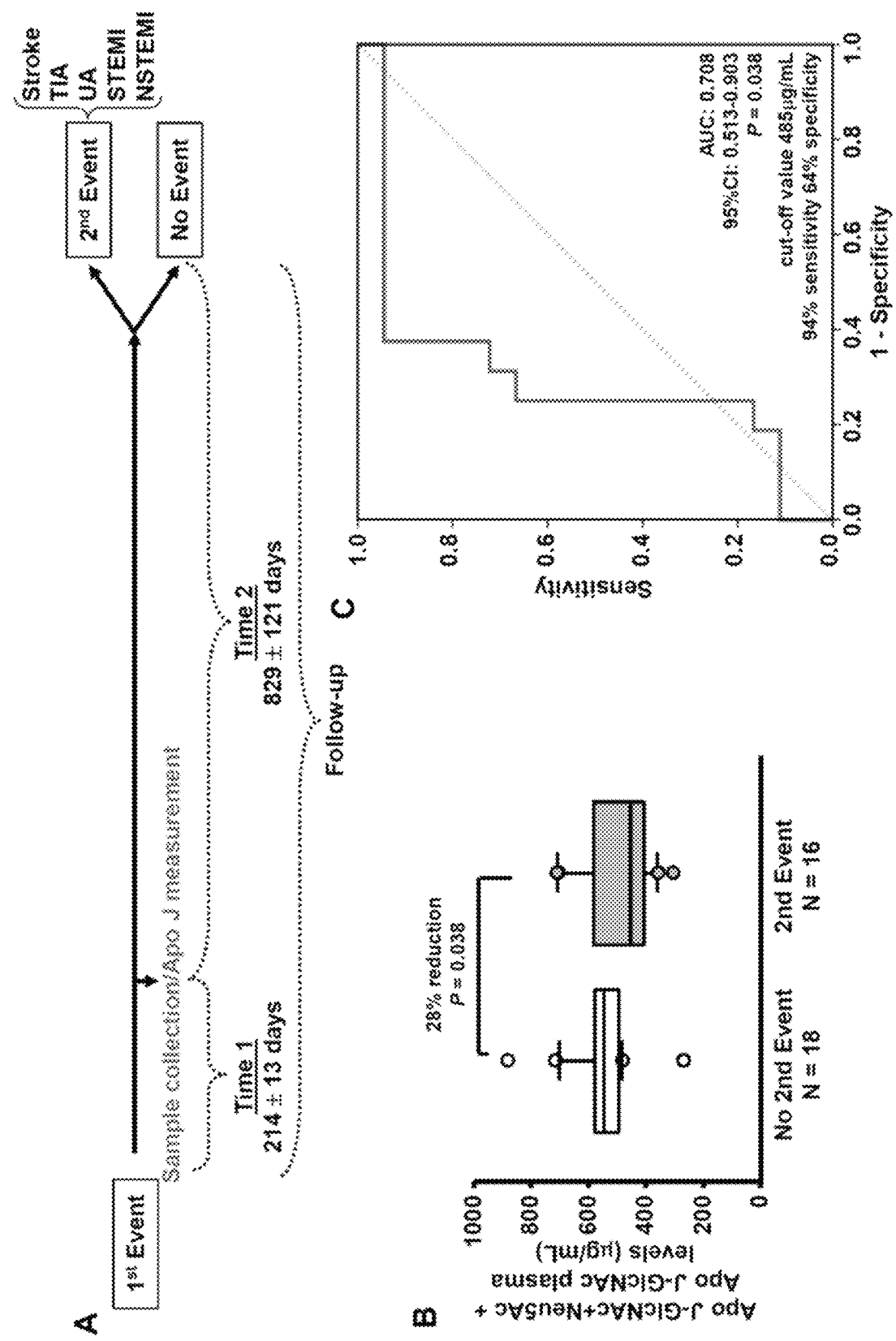

FIG. 11. Predictive Value of Apo J-GlcNAc+Neu5Ac+Apo J-GlcNAc Plasma Levels.

(A) Scheme showing the timings for sample collection and follow-up of stable CAD patients: patients suffered a acute coronary syndrome (ACS) a mean of 0.6±0.04 years before sample collection and were followed-up for 2.3±0.3 years afterwards. (B) Box-plot showing Apo J-GlcNAc+Neu5Ac+Apo J-GlcNAc levels in chronic CAD patients who suffered an ischemic recurrent event at follow-up (N=16) compared to those who did not had a recurrent event (N=18). (C) Receiver operating curve (ROC) showing the predictive value of Apo J-GlcNAc+Neu5Ac+Apo J-GlcNAc levels for the presentation of recurrent ischemic events in stable CAD patients.

Figure 12:
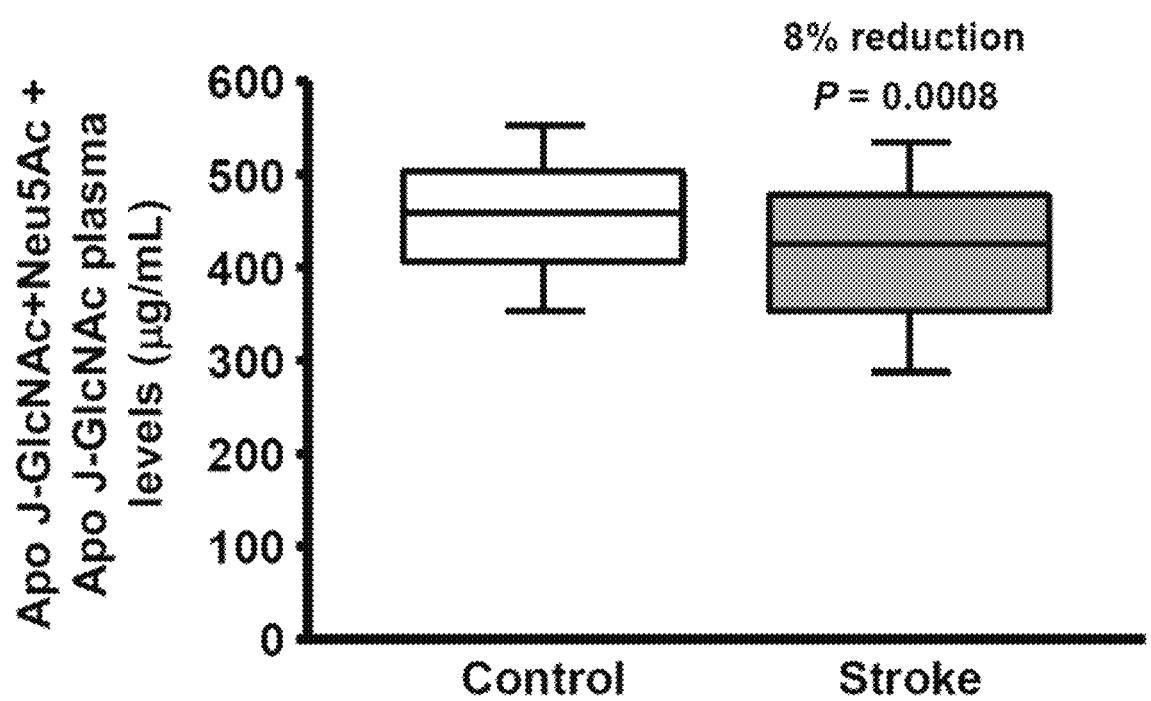

FIG. 12. Diagnostic Value of Apo J-GlcNAc+Neu5Ac+Apo J-GlcNAc in Cerebral Ischemia.

Box-plot showing Apo J-GlcNAc+Neu5Ac+Apo J-GlcNAc plasma levels in stroke patients (N=174) and in healthy subjects (N=164).

DETAILED DESCRIPTION OF THE INVENTION

Diagnostic Methods for Ischemia Tissue Damage

The authors of the present invention have observed that the levels of Apo J-containing GlcNAc residues or the levels of Apo J-containing GlcNAc and sialic acid (Neu5Ac) levels in the early phase of ischemia are decreased with respect to the levels observed in control subjects. While a correlation between the levels of glycosylated Apo J and cardiac ischemia patients has already been described, this study was carried out by determining levels of glycosylated Apo J using a mixture of lectins capable of binding to glycans containing α-mannose, α-glucose, (GlcNAc)$_2$ and Neu5Ac residues. This method did not allow the identification of those forms of glycosylated Apo J which preferentially contributed to the discrimination of patients from control subjects. The authors of the present invention have been able to identify those glycosylated forms of ApoJ which preferentially contribute to the discrimination of samples from patients suffering from ischemia from control samples. In fact, in the previous study authors reported that Apo J-29 was increased in ischemia pre-AMI, contrary to what happens with Apo J-containing GlcNAc residues or Apo J-containing GlcNAc and sialic acid (Neu5Ac). Moreover, ischemia pre-AMI patients depicted a 25% decrease in the detected Apo J with α-mannose, α-glucose, (GlcNAc)$_2$ and Neu5Ac residues, whereas the specific detection of Apo J-containing GlcNAc residues or Apo J-containing GlcNAc and sialic acid (Neu5Ac) resulted in a 45-50% decrease in ischemia pre-AMI patients. Therefore, the determination of these glycosylated forms of Apo J allows the diagnosis of ischemia with increased sensitivity and specificity with respect to the diagnosis carried out using the glycosylated Apo J forms determined using the method described in the prior art.

Accordingly, in a first aspect, the present invention relates to a method (hereinafter the diagnostic method of the invention) for the diagnosis of ischemia or ischemic tissue damage in a subject comprising determining in a sample of said subject the levels of glycosylated Apo J containing N-acetylglucosamine (GlcNAc) residues or the levels of glycosylated Apo J containing N-acetylglucosamine (GlcNAc) and sialic acid residues, wherein decreased levels of Apo J containing N-acetylglucosamine residues with respect to a reference value or decreased levels of Apo J containing N-acetylglucosamine (GlcNAc) and sialic acid residues with respect to a reference value are indicative that the patient suffers ischemia or ischemic tissue damage. The invention also relates to a second method for the diagnosis of ischemia or ischemic tissue damage in a subject comprising determining in a sample of said subject the levels of glycosylated Apo J which is capable of specifically binding to the *Datura stramonium* lectin or the levels of glycosylated Apo J which is capable of specifically binding to the *Triticum vulgaris* lectin, wherein decreased levels of Apo J capable of specifically binding to the *Datura stramonium* lectin or decreased levels of Apo J capable of specifically binding to *Triticum vulgaris* lectin with respect to a reference value are indicative that the patient suffers ischemia or ischemic tissue damage.

The diagnostic method of the invention is particularly advantageous as it allows the detection of an acute ischemic event previous to the irreversible necrotic damage of the related organ or tissue (independently of troponin levels in the case of ACS). This provides a diagnostic value for the presence of ischemia even within the first six hours after the onset of the event.

In the context of the present invention, the term "diagnosis" relates to the ability to discriminate between samples from patients with myocardial or cerebral ischemia or ischemic tissue damage associated thereto and samples from individuals who have not suffered this injury and/or damage, when applied a method as disclosed herein. This detection as it is understood by one skilled in the art is not intended to be 100% correct for all the samples. However, it requires that a statistically significant number of samples analyzed are classified correctly. The amount that is statistically significant can be set by an expert in the field by using different statistical tools, for example, but not limited by the determination of confidence intervals, p value determination, Student's t test and discriminating function Fisher. Preferably, the confidence intervals are at least 90%, at least 95%, at least 97%, at least 98% or less than 99%. Preferably, the p value is less than 0.05, 0.01, 0.005 or 0.0001. Preferably, the present invention can correctly detect ischemia or ischemic damage in at least 60%, at least 70%, by at least 80%, or at least 90% of the subjects of a particular group or population tested.

The term "ischemia" is used herein interchangeably with "ischemic event" and refers to any situation resulting from a decrease or interruption of blood flow to an organ of tissue. Ischemia may be transient or permanent.

The expressions "ischemic tissue damage", "ischemic tissue injury," "tissue damage due to ischemia," "tissue damage associated with ischemia," "tissue damage as a result of ischemia," "tissue damaged caused by ischemia," and "ischemic-damaged tissue" refers to morphological, physiological, and/or molecular damage to an organ or tissue or cell as a result of a period of ischemia.

In one embodiment, the damage caused by ischemia is a damage of the cardiac tissue. In a still more preferred embodiment, the damage to the cardiac tissue is caused by myocardial ischemia.

The term "myocardial ischemia" refers to circulatory disturbances caused by coronary atherosclerosis and/or inadequate oxygen supply to the myocardium. For example, an acute myocardial infarction represents an irreversible ischemic insult to myocardial tissue. This insult results in an occlusive (e.g., thrombotic or embolic) event in the coronary circulation and produces an environment in which the myocardial metabolic demands exceed the supply of oxygen to the myocardial tissue.

In yet another embodiment, the damage is caused by a microvascular angina. The term "microvascular angina", as used herein, refers to a condition resulting from inadequate blood flow through the small cardiac blood vessels.

In one embodiment, the damage caused by ischemia is a damage of the cerebral tissue. In a another embodiment, the damage to the cerebral tissue is caused by ischemic stroke The term "ischemic stroke" refers to a sudden loss of brain function caused by a blockage or a blood vessel to the brain (resulting in the lack of oxygen to the brain), characterized by loss of muscular control, diminution or loss of sensation or consciousness, dizziness, slurred speech, or other symptoms that vary with the extent and the severity of the damage to the brain, also called cerebral accident, or cerebrovascular accident. The term "cerebral ischemia" (or "stroke") also refers to a deficiency in blood supply to the brain, often resulting in a lack of oxygen to the brain.

The term "subject", or "individual" or "animal" or "patient" includes any subject, particularly a mammalian subject, for whom therapy is desired. Mammalian subjects include humans, domestic animals, farm animals, and zoo or pet animals such as dogs, cats, guinea pigs, rabbits, rats, mice, horses, cattle, cows, and so on. In a preferred embodiment of the invention, the subject is a mammal. In a more preferred embodiment of the invention, the subject is a human.

The term "sample" or "biological sample", as used herein, refers to biological material isolated from a subject. The biological sample contains any biological material suitable for detecting levels of glycosylated forms of a given protein, e.g. Apo J. The sample can be isolated from any suitable tissue or biological fluid such as, for example blood, saliva, plasma, serum, urine, cerebrospinal liquid (CSF) or feces. In a particular embodiment of the invention, the sample is a tissue sample or a biofluid. In a more particular embodiment of the invention, the biofluid is selected from the group consisting of blood, serum or plasma.

Preferably, the sample which is used for the determination of the levels of the different glycosylated forms of Apo J is the same type of sample used for determining the reference value in case that the determination is done in relative terms. By way of an example, if the determination of Apo J-containing GlcNAc residues or of Apo J-containing GlcNAc and sialic acid residues is carried out in a plasma sample, then a plasma sample will also be used to determine the reference value. If the sample is a biofluid, then the reference sample will also be determined in the same type of biofluid, e.g. blood, serum, plasma, cerebrospinal fluid.

The term "Apo J", as used herein, refers to a polypeptide also known as "clusterin", "testosterone-Repressed Prostate Message", "Apolipoprotein J", "complement-Associated Protein SP-40,40", "complement cytolysis inhibitor", complement Lysis Inhibitor", "sulfated glycoprotein", "Ku70-Binding Protein", "NA1/NA2", "TRPM-2", "KUB1", "CLI". Human Apo J is the polypeptide provided under accession number P10909 in the UniProtKB/Swiss-Prot database (Entry version 187 of 16 Mar. 2016).

The term "Apo J containing GlcNAc residues", as used herein, refers to any Apo J molecule containing at least one repeat of GlcNAc in at least one glycan chain, although typically, the Apo J will contain at least one N-acetyl glucosamine in each glycan chain. "Apo J containing GlcNAc residues" include Apo J molecules containing at least one GlcNAc residue in high-mannose N-glycans, complex-type N-glycans, hybrid oligosaccharides N-glycans or O-glycans. Depending on the type of N-glycans, the GlcNAc may be found directly attached to the polypeptide chain or in a distal position in the N-glycan.

The term "GlcNAc" or "N-acetyl glucosamine" refers to a derivative of glucose resulting from the amidation of glucosamine by acetic acid and having the general structure:

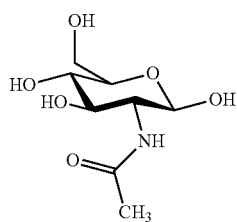

In one embodiment, the Apo J-containing GlcNAc residues contains two residues of GlcNAc and is referred herein as $(GlcNAc)_2$. Apo J molecules containing $(GlcNAc)_2$ residues includes molecules wherein the $(GlcNAc)_2$ is found in high-mannose N-glycans, in complex-type N-glycans, in hybrid oligosaccharides N-glycans or in O-glycans. Depending on the type of N-glycans, the $(GlcNAc)_2$ may be found directly attached to the polypeptide chain or in a distal position in the N-glycan.

In a preferred embodiment, the level of glycosylated Apo J containing GlcNAc or $(GlcNac)_2$ residues is defined as the level of Apo J capable of specifically binding to the *Datura stramonium* lectin.

The term "specific binding", when used in the present invention to refer to the binding of a lectin to a glycosylated form of Apo J is understood as the capacity of the lectin to bind specifically to glycosylated form of Apo J by means of the existence of complementarity between the three-dimensional structures of the two molecules with a substantially higher affinity for non-specific binding such that the binding between said lectin and glycosylated form of Apo J preferably takes place before the binding of any of said molecules with respect to the other molecules present in the reaction mixture. This results in that the lectin does not cross-react with other glycans which may or may not be present in the Apo J molecule. Cross-reactivity of a lectin under investigation may be tested, for example, by assessing binding of said lectin under conventional conditions to the glycan of interest as well as to a number of more or less (structurally and/or functionally) closely related glycan. Only if the lectin binds to the glycan of interest but does not or does not essentially bind to any of the other glycans is considered specific for the glycan of interest. For instance, a binding can be considered specific if the binding affinity between the lectin and the glycosylated Apo J has a dissociation constant (Kd) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M or less than $10^{-15}$ M.

In a preferred embodiment, the "Apo J-containing GlcNAc residues" is substantially free of other types of N-linked or O-linked carbohydrates. In one embodiment, the "Apo J containing GlcNAc residues" does not contain N-linked or O-linked α-mannose residues. In another embodiment, the "Apo J-containing GlcNAc residues" does not contain N-linked or O-linked α-glucose residues. In yet another embodiment, the "Apo J-containing GlcNAc residues" does not contain N-linked or O-linked α-mannose residues or N-linked or O-linked α-glucose residues.

The term "Apo J-containing GlcNAc and sialic acid residues", as used herein, refers to any Apo J molecule containing at least one repeat of N-acetyl-glucose in its glycan chain and at least one repeat of sialic acid residue.

The term "sialic acid", as used herein, refers to the monosaccharide known as N-acetylneuraminic acid (Neu5Ac) and having the general structure

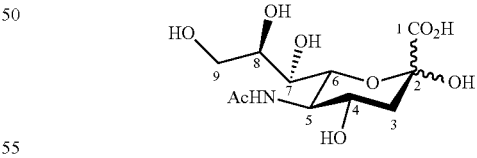

In one embodiment, the Apo J contains two residues of GlcNAc and one sialic acid residue (hereinafter referred to $(GlcNAc)_2$-Neu5Ac). In another embodiment, the GlcNAc and sialic acid residues are connected by virtue of one or more monosaccharides.

In one embodiment, the levels of glycosylated Apo J containing N-acetylglucosamine (GlcNAc) and sialic acid residues correspond to the levels of Apo J capable of specifically binding to the *Triticum vulgaris* lectin.

In a preferred embodiment, the "Apo J-containing GlcNAc residues and sialic acid residues" is substantially free of other types of N-linked or O-linked carbohydrates. In one embodiment, the "Apo J-containing GlcNAc and sialic acid residues" does not contain N-linked or O-linked α-mannose residues. In another embodiment, the "Apo J-containing GlcNAc and sialic acid residues" does not contain N-linked or O-linked α-glucose residues. In yet another embodiment, the "Apo J-containing GlcNAc residues and sialic acid residues" does not contain N-linked or O-linked α-mannose residues or N-linked or O-linked α-glucose residues.

In a preferred embodiment, the "glycosylated Apo J capable of specifically binding to the *T. vulgaris* lectin" corresponds to any glycosylated form of Apo J containing at least one sialic acid residue or at least one GlcNAc residue, including Apo J containing N-acetylglucosamine (GlcNAc) residues but not sialic acid residues, Apo J containing $(GlcNAc)_2$ residues but not sialic acid residues, Apo J containing N-acetylglucosamine (GlcNAc) residues and sialic acid residues, Apo J containing $(GlcNAc)_2$ residues and sialic acid as well as Apo J containing sialic acid but not GlcNAc or $(GlcNAc)_2$ residues. It will be understood that the (GlcNAc) residues and $(GlcNAc)_2$ residues can be found in the same glycan chain than the sialic acid residues. Alternatively, the sialic acid residues can be found in glycan chains not containing (GlcNAc) residues or $(GlcNAc)_2$ residues.

In a preferred embodiment, the "glycosylated Apo J capable of specifically binding to the *D. stramonium* lectin" corresponds to any glycosylated form of Apo J containing at least one GlcNAc residue, including Apo J containing N-acetylglucosamine (GlcNAc) residues and Apo J containing $(GlcNAc)_2$ residues.

The term "decreased levels" or "low levels", in relation to the levels of glycosylated Apo J containing N-acetylglucosamine (GlcNAc) residues relates to any level of expression of Apo J containing N-acetylglucosamine (GlcNAc) residues in a sample lower than the reference value. Thus, the Apo J containing N-acetylglucosamine (GlcNAc) residues expression levels are considered to be decreased or to be lower than its reference value when it is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or more lower than its reference value.

The term "decreased levels" or "low levels", in relation to the levels of glycosylated Apo J containing N-acetylglucosamine (GlcNAc) and sialic acid residues relates to any level of expression of Apo J containing N-acetylglucosamine (GlcNAc) and sialic acid residues in a sample lower than the reference value. Thus, the Apo J containing N-acetylglucosamine (GlcNAc) and sialic acid residues expression levels are considered to be decreased or to be lower than its reference value when it is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or more lower than its reference value.

The term "decreased levels" or "low levels", in relation to the levels of glycosylated Apo J capable of specifically binding to the *T. vulgaris* lectin relates to any level of expression of Apo J capable of specifically binding to the *T. vulgaris* lectin in a sample lower than the reference value. Thus, the expression levels of Apo J capable of specifically binding to the *T. vulgaris* lectin are considered to be decreased or to be lower than its reference value when it is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or more lower than its reference value.

The term "decreased levels" or "low levels", in relation to the levels of glycosylated Apo J capable of specifically binding to the *D. stramonium* lectin relates to any level of expression of Apo J capable of specifically binding to the *D. stramonium* lectin in a sample which is lower than the reference value. Thus, the Apo J capable of specifically binding to the *D. stramonium* lectin expression levels are considered to be decreased or to be lower than its reference value when it is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or more lower than its reference value.

The diagnostic method of the invention comprises comparing the levels obtained in the subject under study with a reference value, whereby decreased levels of Apo J containing N-acetylglucosamine residues with respect to a reference value or decreased levels of Apo J containing N-acetylglucosamine (GlcNAc) and sialic acid residues with respect to a reference value are indicative that the patient suffers ischemia or ischemic tissue damage. The diagnostic method of the invention alternatively comprises comparing the levels obtained in the subject under study with a reference value, whereby decreased levels of Apo J capable of binding to the *D. stramonium* lectin with respect to a reference value or decreased levels of Apo J capable of binding to the *T. vulgaris* lectin with respect to a reference value are indicative that the patient suffers ischemia or ischemic tissue damage.

The term "reference value", as used herein, relates to a predetermined criteria used as a reference for evaluating the values or data obtained from the samples collected from a subject. The reference value or reference level can be an absolute value; a relative value; a value that has an upper or a lower limit; a range of values; an average value; a median value; a mean value; or a value as compared to a particular control or baseline value. A reference value can be based on an individual sample value, such as for example, a value obtained from a sample from the subject being tested, but at an earlier point in time. The reference value can be based on a large number of samples, such as from population of subjects of the chronological age matched group, or based on a pool of samples including or excluding the sample to be tested. In one embodiment, the reference value corresponds to the levels of Apo J-containing GlcNAc residues, to the levels of Apo J-containing GlcNAc and sialic acid (Neu5Ac), the levels of Apo J capable of specifically binding to the *T. vulgaris* lectin or to the levels of Apo J capable of specifically binding to the *D. stramonium* lectin determined in a healthy subject, whereby a healthy subject is understood as a subject that shows no ischemic tissue damage at the moment the levels of Apo J-containing GlcNAc residues, the levels of Apo J-containing GlcNAc and sialic acid (Neu5Ac), the levels of Apo J capable of specifically binding to the *T. vulgaris* lectin or to the levels of Apo J capable of specifically binding to the *D. stramonium* lectin are determined and that, preferably, shows no history of ischemic damage.

In another embodiment, the reference value corresponds to an average or mean level of the corresponding biomarker determined from a pool of samples obtained from a group of patients who are well documented from the clinical point of view, and who present no disease, particularly who are not suffering from ischemic tissue damage, particularly not suffering from ischemic myocardial damage or ischemic cerebral damage. In said samples, the expression levels can be determined, for example by means of the determination of the average expression level in a reference population. In the determination of the reference value, it is necessary to take into consideration some characteristics of the type of sample, such as age, gender, the physical state or other characteristics of the patient. For example, the reference sample can be obtained from identical amounts of a group of at least 2, at least 10, at least 100 to more than 1000 individuals, such that the population is statistically significant.

It will be understood that the reference value used for the diagnosis of patients according to the diagnostic method of the invention is a value obtained from the same type of sample and of the same biomarker as the marker which is being considered in the diagnosis. Accordingly, if the diagnostic method is carried out by determining the levels of glycosylated Apo J containing GlcNAc or (GlcNAc)$_2$, then the reference value used in the diagnosis is also the expression level of glycosylated Apo J containing GlcNAc residues or (GlcNAc)$_2$, as the case may be, obtained from a healthy subject or from a pool of samples as defined above. In another embodiment, if the diagnostic method is carried out by determining the levels of glycosylated Apo J containing GlcNAc and sialic acid residues, then the reference value used in the diagnosis is also the expression level of glycosylated Apo J containing N-acetylglucosamine (GlcNAc) and sialic acid residues obtained as explained above. In another embodiment, if the diagnostic method is carried out by determining the levels of glycosylated Apo J which is capable of specifically binding to the *D. stramonium* lectin, then the reference value used in the diagnosis is also the expression level of glycosylated Apo J capable of specifically binding to the *D. stramonium* lectin obtained as explained above. In another embodiment, if the diagnostic method is carried out by determining the levels of glycosylated Apo J which is capable of specifically binding to the *T. vulgaris* lectin, then the reference value used in the diagnosis is also the expression level of glycosylated Apo J capable of specifically binding to the *T. vulgaris* obtained as explained above.

In another embodiment, if the biomarker is determined in order to diagnose myocardial tissue damage, the reference value will be the levels of the same biomarker from a healthy subject who does not show myocardial tissue damage and who preferably has no record of suffering myocardial tissue damage. If the reference value is the average level of the same biomarker obtained from a pool of samples from subjects, then the subjects from which the pool of samples is prepared are subjects who do not show myocardial tissue damage and who preferably have no record of suffering myocardial tissue damage.

In another embodiment, if the biomarker is determined in order to diagnose cerebral tissue damage, the reference value will be the levels of the same biomarker from a healthy subject who does not show cerebral tissue damage and who preferably has no record of suffering cerebral tissue damage. If the reference value is the average level of the same biomarker obtained from a pool of samples from subjects, then the subjects from which the pool of samples are obtained are subjects who do not show cerebral tissue damage and who preferably have no record of suffering cerebral tissue damage.

The reference value used in the diagnostic method of the invention can be optimized in order to obtain a desired specificity and sensitivity.

In one embodiment, the reference value used in the diagnosis of myocardial ischemia is of 332 µg/mL of Apo J-GlcNAc+Neu5Ac+Apo J-GlcNAc or of 393 µg/mL of Apo J-GlcNac when a sensitivity of 97% and a specificity of 71% is desired or of 393 µg/mL of Apo J-GlcNAc when a sensitivity of 81% and a specificity of 72% is desired (i.e. the diagnostic method according to the present invention allows the diagnosis of myocardial ischemia with sensitivity of 97% and a specificity of 71% when a patient shows less than 332 µg/mL of Apo J-GlcNAc+Neu5Ac+Apo J-GlcNAc or with a sensitivity of 81% and a specificity of 72% when a patient shows less than 393 µg/mL Apo J-GlcNAc).

In another embodiment, the reference value used in the diagnosis of cerebral ischemia is of 424 µg/mL of Apo J-GlcNAc+Neu5Ac+Apo J-GlcNAc when a sensitivity of 66% and a specificity of 51% is desired (i.e. the diagnostic method according to the present invention allows the diagnosis of cerebral ischemia with a sensitivity of 66% and a specificity of 51% when a patient shows less than 424 µg/mL Apo J-GlcNAc+Neu5Ac+Apo J-GlcNAc).

In one embodiment, the reference value used in the diagnosis of myocardial ischemia is of 332 µg/mL of Apo J capable of binding to the *T. vulgaris* lectin when a sensitivity of 97% and a specificity of 71% is desired or of 393 µg/mL of Apo J capable of binding to the *D. stramonium* lectin when a sensitivity of 81% and a specificity of 72% is desired (i.e. the diagnostic method according to the present invention allows the diagnosis of myocardial ischemia with sensitivity of 97% and a specificity of 71% when a patient shows less than 332 µg/mL of Apo J capable of binding to the *T. vulgaris* lectin or with a sensitivity of 81% and a specificity of 72% when a patient shows less than 393 µg/mL Apo J capable of binding to the *D. stramonium* lectin).

In another embodiment, the reference value used in the diagnosis of cerebral ischemia is of 424 µg/mL of Apo J capable of binding to the *T. vulgaris* lectin when a sensitivity of 66% and a specificity of 51% is desired (i.e. the diagnostic method according to the present invention allows the diagnosis of cerebral ischemia with a sensitivity of 66% and a specificity of 51% when a patient shows less than 424 µg/mL Apo J capable of binding to the *T. vulgaris* lectin).

In a preferred embodiment, the determination of the levels of glycosylated Apo J containing N-acetylglucosamine (GlcNAc), the levels of glycosylated Apo J containing N-acetylglucosamine (GlcNAc) and sialic acid residues, the levels of Apo J which is capable of specifically binding to the *D. stramonium* lectin or the levels of glycosylated Apo J which is capable of specifically binding to the *T. vulgaris* lectin is carried out before a detectable increase in necrosis marker can be detected in the sample. In a preferred embodiment, the necrosis marker is either T-troponin or CK. In yet another embodiment, the determination of the levels of glycosylated Apo J containing N-acetylglucosamine (GlcNAc), of the levels of glycosylated Apo J containing N-acetylglucosamine (GlcNAc) and sialic acid residues, of the levels of Apo J which is capable of specifically binding to the *D. stramonium* lectin or of the levels of glycosylated Apo J which is capable of specifically binding to the *T.*

*vulgaris* lectin is carried out in a sample obtained within 1 hour, 2 hours, 3 hours, 4 hours, 5 hours, 6 hours, 7 hours, 8 hours, 9 hours, 10 hours, 12 hours, 14 hours, 16 hours, 18 hours, 20 hours, 30 hours, 40 hours, 50 hours or more of the onset of the symptoms of ischemia damage. In a preferred embodiment, in the case of myocardial ischemic damage, symptoms are usually chest pain, shortness of breath, diaphoresis, weakness, light-headedness, nausea, vomiting, and palpitations. In one embodiment, the patient is a pre-AMI patient.

In another preferred embodiment, in the case of cerebral ischemic damage, the symptom of ischemia damage is, without limitation, altered smell, taste, hearing, or vision, ptosis or weakness of ocular muscles, decreased reflexes: gag, swallow, pupil reactivity to light, decreased sensation and muscle weakness of the face, balance problems and nystagmus, aphasia, apraxia (altered voluntary movements), visual field defects, dysarthria, memory deficits, hemineglect, disorganized thinking, confusion, hypersexual gestures (with involvement of frontal lobe), lack of insight of his or her, usually stroke-related, disability, altered walking gait, altered movement coordination, vertigo or disequilibrium.

In another embodiment, the determination of the levels of the glycosylated forms of Apo J according to the diagnostic method of the invention is carried out in a sample from the patient which has been obtained before the patient has been administered with any medicament aimed at reducing ischemia or reducing the ischemic tissue damage. In one embodiment, in the case of myocardial tissue damage, the determination of the levels of the glycosylated forms of Apo J is carried out in a sample from the patient which has been obtained before the patient has been treated with statins, anti-platelets and/or anti-coagulants.

In one embodiment, in the case of cerebral tissue damage, the determination of the levels of the glycosylated forms of Apo J is carried out in a sample from the patient which has been obtained before the patient has been treated with tissue plasminogen activator, anti-platelets and/or anti-coagulants.

Method for the Prognosis of Patients Having Suffered Ischemic Damage

The authors of the present invention have also found that, unexpectedly, the levels of glycosylated Apo J are useful not only for the detection of an ongoing ischemic event, but also for the prognosis of a patient which has suffered an ischemic event.

Thus, in another aspect, the invention relates to a method for predicting the progression of ischemia in a patient (hereinafter prognostic method of the invention) having suffered an ischemic event or for determining the prognosis of a patient having suffered an ischemic event, comprising determining in a sample of said patient the levels of glycosylated Apo J, wherein decreased levels of glycosylated Apo J with respect to a reference value are indicative that the ischemia is progressing or of a poor prognosis of the patient.

In the context of the present invention, the term "predicting the progression" relates to the ability to predict the course of the disease after suffering ischemia or ischemic tissue damage associated thereto when applied a method as disclosed herein. This detection, as understood by one skilled in the art, is not intended to be 100% correct for all the samples. However, it requires that a statistically significant number of analyzed samples have to be classified correctly. The amount that is statistically significant can be set by an expert in the field by using different statistical tools, for example, but not limited by the determination of confidence intervals, p value determination, Student's t test and discriminating function Fisher. Preferably, the confidence intervals are at least 90%, at least 95%, at least 97%, at least 98% or less than 99%. Preferably, the p value is less than 0.05, 0.01, 0.005 or 0.0001. Preferably, the present invention can correctly detect ischemia or ischemic damage in at least 60%, at least 70%, by at least 80%, or at least 90% of the subjects of a particular group or population tested.

In the context of the present invention, the term "determining the prognosis" is used interchangeably with "prognosis" relates to the ability to predict the outcome of patients after suffering myocardial or cerebral ischemia or ischemic tissue damage associated thereto when applied a method as disclosed herein. This detection as understood by one skilled in the art is not intended to be 100% correct for all the samples. However, it requires that a statistically significant number of analyzed samples are classified correctly. The amount that is statistically significant can be set by an expert in the field by using different statistical tools, for example, but not limited by the determination of confidence intervals, p value determination, Student's t test and discriminating function Fisher. Preferably, the confidence intervals are at least 90%, at least 95%, at least 97%, at least 98% or less than 99%. Preferably, the p value is less than 0.05, 0.01, 0.005 or 0.0001. Preferably, the present invention can correctly detect ischemia or ischemic damage in at least 60%, at least 70%, by at least 80%, or at least 90% of the subjects of a particular group or population tested.

In a preferred embodiment, the prognosis of the patient is determined as the risk of 6 months recurrence. In the case of determining the risk of 6 months recurrence, it will be understood that recurrence refers to a second ischemic event occurring within the first 6 months after the first ischemic event. In one embodiment, the second ischemic event is of the same type as the first ischemic event, i.e. the first ischemic event is a myocardial ischemia and prognosis is determined as the risk that the patient suffers a second myocardial ischemic event. In another embodiment, the second ischemic event is of a different type as the first ischemic event, i.e. if the first ischemic event is a myocardial ischemia, then prognosis is determined as the risk that the patient suffers a cerebral ischemic event or vice versa, if the first ischemic event is a cerebral ischemic event, then prognosis is determined as the risk that the patient suffers a myocardial ischemic event.

In another embodiment, the prognosis of the patient is determined as the risk of in-hospital mortality.

In a preferred embodiment, the prognosis of the patient is determined as the risk of 6-months mortality.

The terms "Apo J", "patient", "ischemic event" and "sample" have been described in detail in the context of the diagnostic method of the invention and are equally applicable to the present method.

In one embodiment, the sample is a biofluid. In another embodiment, the biofluid is plasma or serum.

In one embodiment, the ischemic event is a myocardial ischemic event. In yet another embodiment, the myocardial ischemic event is a ST-elevation myocardial infarction (STEMI). In another embodiment, the ischemic event is a cerebral ischemic event.

The term "glycosylated Apo J", as used herein, refers to any form of Apo J which contains at least one N-linked or O-linked oligosaccharide chain attached to the polypeptide chain. The term "glycosylated Apo J" includes both variants containing N-linked and O-linked oligosaccharides. The term also includes Apo J containing N-linked complex type oligosaccharides, high mannose oligosaccharides or hybrid-type oligosaccharides.

In one embodiment, the glycosylated Apo J which is determined in the prognostic method of the invention is glycosylated Apo J containing N-acetylglucosamine (GlcNAc) residues. In a yet more preferred embodiment, the level of glycosylated Apo J containing N-acetylglucosamine (GlcNAc) residues correspond to the level of Apo J capable of specifically binding to the *Datura stramonium* lectin. In one embodiment, the glycosylated Apo J which is determined in the prognostic method of the invention is glycosylated Apo J which is capable of specifically binding to the *Datura stramonium* lectin.

In another embodiment, the glycosylated Apo J determined in the prognostic method of the invention is glycosylated Apo J containing N-acetylglucosamine (GlcNAc) and sialic acid residues. In a yet more preferred embodiment, the levels of glycosylated Apo J containing N-acetylglucosamine (GlcNAc) and sialic acid residues correspond to the levels of Apo J capable of specifically binding to the *Triticum vulgaris* lectin. In one embodiment, the glycosylated Apo J which is determined in the prognostic method of the invention is glycosylated Apo J which is capable of specifically binding to the *Triticum vulgaris* lectin.

The terms "decreased levels" or "low levels", in relation to the levels of glycosylated Apo J relates to any level of expression of glycosylated Apo J in a sample which is lower than the reference value. Thus, glycosylated Apo J levels are considered to be decreased or to be lower than its reference value when it is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or more lower than its reference value. In a preferred embodiment, the levels of glycosylated Apo J containing N-acetylglucosamine (GlcNAc) residues are lower than those found in a reference sample. In another embodiment, the levels of glycosylated Apo J containing N-acetylglucosamine $(GlcNAc)_2$ residues are lower than those found in a reference sample. In another embodiment, the levels of glycosylated Apo J capable of specifically binding to the *T. vulgaris* lectin are lower than those in a reference sample. In another embodiment, the levels of glycosylated Apo J capable of specifically binding to the *D. stramonium* lectin are lower than those in a reference sample.

The term "reference value", when referred to the prognostic method of the invention, relates to a predetermined criteria used as a reference for evaluating the values or data obtained from the samples collected from a subject. The reference value or reference level can be an absolute value; a relative value; a value that has an upper or a lower limit; a range of values; an average value; a median value; a mean value; or a value as compared to a particular control or baseline value. A reference value can be based on an individual sample value, such as for example, a value obtained from a sample from the subject being tested, but at an earlier point in time. The reference value can be based on a large number of samples, such as from population of subjects of the chronological age matched group, or based on a pool of samples including or excluding the sample to be tested. In one embodiment, the reference value corresponds to the levels of glycosylated Apo J determined in a subject who has suffered an ischemic event and in which the ischemia has not progressed or who has had a good progression. In the case of progression determined as the risk of 6 months recurrence, the reference value can be taken as the glycosylated Apo J levels in a sample from a patient taken at the moment of the ischemic event but wherein the patient has not suffered any further ischemic event at least 6 months, 7 months, 8 months, 9 months, 10 month, 11 months, 12 months, 18 months, 24 months, 36 months, 48 months or more after the first ischemic event. In another embodiment, when the progression is determined as the risk of in hospital mortality, the reference value can be taken as the levels of glycosylated Apo J in a patient at the moment of the ischemic event but wherein the patient has been released from the hospital. In the case of progression determined as the risk of 6 months mortality, the reference value can be taken as the glycosylated Apo J levels in a sample from a patient taken at the moment of the ischemic event but wherein the patient is still alive at least 6 months, 7 months, 8 months, 9 months, 10 month, 11 months, 12 months, 18 months, 24 months, 36 months, 48 months or more after the ischemic event.

In another embodiment, the reference value corresponds to an average or mean level of the corresponding biomarker determined from a pool of samples obtained from a group of patients who are well documented from the clinical point of view, and who, after having suffered an ischemic event, have shown a good prognosis as defined in the previous paragraph. In said samples, the expression levels can be determined, for example by means of the determination of the average expression level in a reference population. In the determination of the reference value, it is necessary to take into consideration some characteristics of the type of sample, such as age, gender, the physical state and other characteristics of the patient. For example, the reference sample can be obtained from identical amounts of a group of at least 2, at least 10, at least 100 to more than 1000 individuals, such that the population is statistically significant.

It will be understood that the reference value used for the prognosis of patients according to the prognostic method of the invention is a value obtained from the same type of sample and of the same biomarker as the marker which is being considered in the diagnosis. Accordingly, if the prognostic method is carried out by determining the levels of glycosylated Apo J containing GlcNAc or $(GlcNAc)_2$, then the reference value used in the prognosis is also the expression level of glycosylated Apo J containing GlcNAc residues or $(GlcNAc)_2$, as the case may be, obtained from a healthy subject or from a pool of samples as defined above. In another embodiment, if the prognosis method is carried out by determining the levels of glycosylated Apo J containing GlcNAc and sialic acid residues, then the reference value used in the prognosis is also the expression level of glycosylated Apo J containing N-acetylglucosamine (GlcNAc) and sialic acid residues obtained as explained above.

If the prognostic method is carried out by determining the levels of glycosylated Apo J capable of binding to the *D. stramonium* lectin, then the reference value used in the prognosis is also the expression level of glycosylated Apo J capable of binding to the *D. stramonium* lectin obtained from a healthy subject or from a pool of samples as defined above. In another embodiment, if the prognosis method is carried out by determining the levels of glycosylated Apo J capable of binding to the *T. vulgaris* lectin, then the reference value used in the prognosis is also the expression level of glycosylated Apo J capable of binding to the *T. vulgaris* lectin obtained as explained above.

In another embodiment, if the biomarker is determined in order to determine the prognosis of a patient having suffered a myocardial tissue damage, the reference value will be the levels of the same biomarker from a subject who, after having suffered a myocardial ischemic event, has shown a good prognosis according to any of the criteria defined above (lack of recurrence of ischemic event after 6 months, no in-hospital death or mortality after 6 months). If the reference value is the average level of the same biomarker obtained from a pool of samples from subjects, then the subjects from which the pool of samples is prepared are subjects who, after having suffered a myocardial ischemic event, have shown a good prognosis according to any of the criteria defined above (lack of recurrence of ischemic event after 6 months, no in-hospital death or mortality after 6 months)

In another embodiment, if the biomarker is determined in order to determine the prognosis of cerebral tissue damage, the reference value will be the levels of the same biomarker from a subject who, after having suffered a cerebral ischemic event, has shown a good prognosis according to any of the criteria defined above (lack of recurrence of ischemic event after 6 months, no in-hospital death or mortality after 6 months). If the reference value is the average level of the same biomarker obtained from a pool of samples from subjects, then the subjects from which the pool of samples is prepared are subjects who, after having suffered a cerebral ischemic event, have shown a good prognosis according to any of the criteria defined above (lack of recurrence of ischemic event after 6 months, no in-hospital death or mortality after 6 months).

The reference value used in the prognostic method of the invention can be optimized in order to obtain a desired specificity and sensitivity.

In a specific embodiment, the reference value used in the prognosis of mortality and recurrent events is of 287 μg/mL of Apo J-GlcNAc when a sensitivity of 58% and a specificity of 51% is desired (i.e. the prognostic method according to the present invention allows the prognosis of mortality or recurrent events with a sensitivity of 58% and a specificity of 61% when a patient shows less than 287 μg/mL Apo J-GlcNAc).

In a specific embodiment, the reference value used in the prognosis of mortality and recurrent events is of 398 μg/mL of Apo J-GlcNAc+Neu5Ac+Apo J-GlcNAc when a sensitivity of 55% and a specificity of 65% is desired (i.e. the prognostic method according to the present invention allows the prognosis of mortality or recurrent events with a sensitivity of 55% and a specificity of 65% when a patient shows less than 398 μg/mL Apo J-GlcNAc+Neu5Ac+Apo J-GlcNAc).

In a specific embodiment, the reference value used in the prognosis of mortality and recurrent events is of 398 μg/mL of Apo J capable of specifically binding to the *T. vulgaris* lectin when a sensitivity of 55% and a specificity of 65% is desired (i.e. the prognostic method according to the present invention allows the prognosis of mortality or recurrent events with a sensitivity of 55% and a specificity of 65% when a patient shows less than 398 μg/mL Apo J capable of specifically binding to the *T. vulgaris* lectin).

In a specific embodiment, the reference value used in the prognosis of mortality and recurrent events is of 287 μg/mL of Apo J capable of specifically binding to the *D. stramonium* lectin when a sensitivity of 58% and a specificity of 51% is desired for the prognosis of mortality and recurrent events and of 273 μg/mL of Apo J capable of specifically binding to the *D. stramonium* lectin when a sensitivity of 64% and a specificity of 50% is desired for the prognosis of mortality (i.e. the prognostic method according to the present invention allows the prognosis of mortality or recurrent events with a sensitivity of 58% and a specificity of 51% when a patient shows less than 287 μg/mL Apo J capable of specifically binding to the *D. stramonium* lectin or the prognosis of mortality with a sensitivity of 64% and a specificity of 50% when a patient shows less than 273 μg/mL Apo J capable of specifically binding to the *D. stramonium* lectin).

Risk Stratification Method of the Invention

The authors of the present invention have also shown that the levels of glycosylated Apo J and, in particular, the level of glycosylated Apo J containing GlcNAc and Neu5Ac is also a useful biomarker for determining the risk that a patient who suffers stable coronary artery disease (CAD) suffers a recurrent ischemic event. This method allows the stratification of patients according to the risk that they suffer ischemic events and thus, is useful for assigning specific preventive therapies to the patients depending on the risk.

Thus, in another aspect, the invention relates to a method for determining the risk (hereinafter, risk stratification method of the invention) that a patient suffering from stable coronary artery disease suffers a recurrent ischemic event, said method comprising determining in a sample of said patient the levels of glycosylated Apo J, wherein decreased levels of glycosylated Apo J with respect to a reference value are indicative that the patient shows an increased risk of suffering a recurrent ischemic event.

In the context of the present invention, the term "determining the risk" or "risk stratification" relates to the ability to determine the risk or probability of: a) suffering additional clinical complications of patients after suffering myocardial or cerebral ischemia or ischemic tissue damage associated thereto, and/or b) benefiting from a specific treatment for myocardial or cerebral ischemia or ischemic tissue damage associated thereto when applied a method as disclosed herein. This detection as it is understood by one skilled in the art is not intended to be 100% correct for all the samples. However, it requires that a statistically significant number of samples analyzed are classified correctly. The amount that is statistically significant can be set by an expert in the field by using different statistical tools, for example, but not limited by the determination of confidence intervals, p value determination, Student's t test and discriminating function Fisher. Preferably, the confidence intervals are at least 90%, at least 95%, at least 97%, at least 98% or less than 99%. Preferably, the p value is less than 0.1, 0.05, 0.01, 0.005 or 0.0001. Preferably, the present invention can correctly detect ischemia or ischemic damage in at least 60%, at least 70%, by at least 80%, or at least 90% of the subjects of a particular group or population tested.

The terms patient, ischemic event, sample, Apo J and glycosylated Apo J have been described in detail in the context of the diagnostic and prognostic method of the invention and are equally applicable to the risk stratification method of the invention.

In one embodiment, the recurrent ischemic event is an acute coronary syndrome, a stroke or a transient ischemic event.

In one embodiment, the sample is a biofluid. In another embodiment, the biofluid is plasma or serum.

In one embodiment, the ischemic event is a myocardial ischemic event. In yet another embodiment, the myocardial ischemic event is a ST-elevation myocardial infarction (STEMI). In another embodiment, the ischemic event is a cerebral ischemic event.

In one embodiment, the glycosylated Apo J which is determined in the prognostic method of the invention is glycosylated Apo J containing N-acetylglucosamine (GlcNAc) residues. In another embodiment, the level of glycosylated Apo J containing N-acetylglucosamine (GlcNAc) residues correspond to the level of Apo J capable of specifically binding to the *Datura stramonium* lectin.

In another embodiment, the glycosylated Apo J determined in the prognostic method of the invention is glycosylated Apo J containing N-acetylglucosamine (GlcNAc) and sialic acid residues. In another embodiment, the levels of glycosylated Apo J containing N-acetylglucosamine (GlcNAc) and sialic acid residues correspond to the levels of Apo J capable of specifically binding to the *Triticum vulgaris* lectin The term "stable coronary disease" and "stable coronary heart disease" have the same meaning and are used interchangeable. Both terms include the medical condition stable coronary artery disease (SCAD). "Stable" in the context of the terms "stable cardiovascular disease", "stable coronary disease" or "stable coronary heart disease" is defined as any conditions of diagnosed cardiovascular disease in the absence of acute cardiovascular events. Hence, e.g. stable coronary disease defines the different evolutionary phases of coronary disease, excluding the situations in, which coronary artery thrombosis dominates clinical presentation (acute coronary syndrome). Patients suffering from SCAD are defined by one or more of the following conditions: stable angina pectoris with positive ECG stress test or positive myocardial scintigraphy or stenosis of >50 percent of coronary artery, history of acute coronary syndrome, history of coronary revascularization, under treatment by anti-platelets, anti-coagulants and/or statins at a stable dose for at least 3 months.

In a preferred embodiment, patients suffering from stable coronary disease had suffered an acute coronary syndrome prior to the stable coronary disease. In preferred embodiments, the patient suffering from stable coronary disease had suffered an acute coronary syndrome at least 1 month, 2 months, 3 months, 4 months, 5 months, 6 months, 7 months, 8 months, 8 months, 9 months, 10 months, 11 months, 12 months, 18 months, 24 months, 36 months, 48 months, 60 months or more prior to the stable coronary disease.

The terms "decreased levels" or "low levels", in relation to the levels of glycosylated Apo J in the prognostic method of the invention relates to any level of expression of glycosylated Apo J in a sample which is lower the a reference value. Thus, glycosylated Apo J levels are considered to be decreased or to be lower than its reference value when it is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or more lower than its reference value. In a preferred embodiment, the levels of glycosylated Apo J containing N-acetylglucosamine (GlcNAc) residues are lower than those found in a reference sample. In another embodiment, the levels of glycosylated Apo J containing N-acetylglucosamine (GlcNAc)$_2$ residues are lower than those found in a reference sample. In another embodiment, the levels of glycosylated Apo J containing Apo J containing N-acetylglucosamine (GlcNAc) and sialic acid residues are lower than those in a reference sample. In another embodiment, the levels of glycosylated Apo J capable of binding to the *T. vulgaris* lectin are lower than those found in a reference sample. In another embodiment, the levels of glycosylated Apo J capable of binding to the *D. stramonium* lectin are lower than those in a reference sample.

The term "reference value", when referred to the risk stratification method of the invention, relates to a predetermined criteria used as a reference for evaluating the values or data obtained from the samples collected from a subject. The reference value or reference level can be an absolute value; a relative value; a value that has an upper or a lower limit; a range of values; an average value; a median value; a mean value; or a value as compared to a particular control or baseline value. A reference value can be based on an individual sample value, such as for example, a value obtained from a sample from the subject being tested, but at an earlier point in time. The reference value can be based on a large number of samples, such as from population of subjects of the chronological age matched group, or based on a pool of samples including or excluding the sample to be tested. In one embodiment, the reference value corresponds to the levels of glycosylated Apo J determined in a subject who suffers stable coronary disease but who has not suffered any recurrent ischemic event. In this case, the suitable patients from which the reference value can be determined are patients who have suffered stable coronary disease and who have not suffered ischemic recurrent events for at least 6 months, 7 months, 8 months, 9 months, 10 month, 11 months, 12 months, 18 months, 24 months, 36 months, 48 months or more after the onset of the stable coronary disease.

In another embodiment, the reference value corresponds to an average or mean level of the corresponding biomarker determined from a pool of samples obtained from a group of patients who are well documented from the clinical point of view, and who suffer stable coronary disease but who have not suffered a recurrent ischemic event events for at least 6 months, 7 months, 8 months, 9 months, 10 month, 11 months, 12 months, 18 months, 24 months, 36 months, 48 months or more after the onset of the stable coronary disease. In said samples, the expression levels can be determined, for example by means of the determination of the average expression level in a reference population. In the determination of the reference value, it is necessary to take into consideration some characteristics of the type of sample, such as age, gender, the physical state and the like of the patient. For example, the reference sample can be obtained from identical amounts of a group of at least 2, at least 10, at least 100 to more than 1000 individuals, such that the population is statistically significant.

It will be understood that the reference value used for the risk stratification of patients according to the risk stratification method of the invention is a value obtained from the same type of sample and of the same biomarker as the marker which is being considered in the diagnosis. Accordingly, if the risk stratification method is carried out by determining the levels of glycosylated Apo J containing GlcNAc or (GlcNAc)$_2$, then the reference value used in the risk stratification is also the expression level of glycosylated Apo J containing GlcNAc residues or (GlcNAc)$_2$, as the case may be, obtained from a subject or from a pool of samples as defined above. In another embodiment, if the risk stratification method is carried out by determining the levels of glycosylated Apo J containing GlcNAc and sialic acid residues, then the reference value used in the risk stratification is also the expression level of glycosylated Apo J containing N-acetylglucosamine (GlcNAc) and sialic acid residues obtained as explained above.

In another embodiment, if the risk stratification method is carried out by determining the levels of glycosylated Apo J capable of specifically binding to the *T. vulgaris* lectin, then the reference value used in the risk stratification is also the expression level of glycosylated Apo J capable of specifically binding to the *T. vulgaris* lectin obtained as explained above. In another embodiment, if the risk stratification method is carried out by determining the levels of glycosylated Apo J capable of specifically binding to the *D. stramonium* lectin, then the reference value used in the risk stratification is also the expression level of glycosylated Apo J capable of specifically binding to the *D. stramonium* lectin obtained as explained above.

The reference value used in the risk stratification method of the invention can be optimized in order to obtain a desired specificity and sensitivity. In a specific embodiment, the reference value used in the risk stratification method is of 485 µg/mL of Apo J-GlcNAc+Neu5Ac+Apo J-GlcNAc when a sensitivity of 94% and a specificity of 64% is desired (i.e. the risk stratification method according to the present invention allows the prediction of recurrent events in patients suffering from CAD with a sensitivity of 94% and a specificity of 64% when a patient shows less than 485 µg/mL Apo J-GlcNAc+Neu5Ac+Apo J-GlcNAc).

In another embodiment, the reference value used in the risk stratification method is of 485 µg/mL of Apo J capable of specifically binding to the *T. vulgaris* lectin when a sensitivity of 94% and a specificity of 64% is desired (i.e. the risk stratification method according to the present invention allows the prediction of recurrent events in patients suffering from CAD with a sensitivity of 94% and a specificity of 64% when a patient shows less than 485 µg/mL Apo J capable of specifically binding to the *T. vulgaris* lectin).

Kits for the Determination of the Biomarkers According to the Invention

The authors of the present invention have also obtained a kit that allows the detection of glycosylated Apo J which is suitable for diagnosis of the diseases mentioned herein as well as other diseases in which glycosylated Apo J is involved.

Thus, in another aspect, the invention relates to a kit comprising a. A first reagent which is a lectin which specifically binds to a glycan residue selected from N-acetylglucosamine and sialic acid and b. A second reagent which is capable of specifically binding to the Apo J polypeptide.

As used in the present invention, the term "lectin which specifically binds to a glycan residue selected from N-acetylglucosamine and sialic acid" refers to any protein different from an antibody with the capacity of binding to sugars coming from any organism as well as variants thereof obtained in a recombinant manner and which maintain the capacity of binding to the sugar residues in glycoproteins. Examples of lectins suitable for use in the present invention include but are not limited to lectins isolated from *Conavalia ensiformis, Anguilla anguilla, Tritium vulgaris, Datura stramonium, Galanthus nivalis, Maackia amurensis, Arachis hypogaea, Sambucus nigra, Erythtina cristagalli, Lens culinaris, Glycine max, Phaseolus vulgaris, Allomyrina dichotoma, Dolichos biflorus, Lotus tetragonolobus, Ulex europaeus*, and *Ricinus communis*.

Examples of lectins suitable for use in the present invention include but are not limited to the lectins shown in Table 1, which indicates the common name of the lectin, the organism which it comes from and the sugar which binds specifically to said lectin.

| Lectin | Origin | Specificity |
|---|---|---|
| Lectin II | *Griffonia simplicifolia* | α or 1β terminal GlcNAc (R) |
| RCA-I | *Ricinus communis* | Terminal GalβGlcNAc-R |
| Wheat germ agglutinin | *Triticum vulgaris* | Terminal sialic acid and terminal GlcNAc |
| LFA | *Limax flavus* | Terminal sialic acid |
| Stramonium agglutinin | *Datura stramonium* | (β-1,4) linked N-acetylglucosamine oligomers, |
| Tomato lectin | *Lycopersicum esculentum* | (Galβ4GlcNAc)n-R |
| MAL/MAA | *Maackia amurensis* | 2-3Galβ3GalNAc-R sialic acid |
| L-PHA | *Phaseolus vulgaris* | tri/tetraantennary N-glycans |
| E-PHA | *Phaseolus vulgaris* | Bisected biantennary N-glycans |
| Elder lectin | *Sambucus nigra* | 2-6Gal/Gal(/GalNAc sialic acid |
| Potato lectin | *Solanum tuberosum* | Long chain (Galβ4GlcNAc)n-R |
| Aleuria aurantia lectin | *Aleuria aurantia* | Fucα1-2Galβ1-4(Fucα1-3/4)Galβ1-4GlcNAc; R$_2$-GlcNAcβ1-4(Fucα1-6)GlcNAc-R$_1$ |
| Alomyrina dichotoma lectin | *Allomyrina dichotoma* | Galβ1-4GlcNAc-R |

In a preferred embodiment the lectin is the lectin from *Triticum vulgaris*, the lectin from *Datura stramonium* or a combination thereof.

In a preferred embodiment, the second reagent is an anti-Apo J antibody or a fragment thereof containing its antigen-binding region.

In the context of the present invention, the term "Apo J antibody" refers to immunoglobulin molecules and immunologically active portions thereof, i.e. molecules that contain an antigen binding site that specifically binds glycosylated Apo J as defined herein. Antibodies suitable for use according to the present invention include antibodies which recognize one or more epitopes located in the polypeptide part of the glycosylated Apo J, provided that the binding is not affected by the presence of N-linked or O-linked carbohydrates. These antibodies are capable of binding both glycosylated forms of Apo J as well as non-glycosylated forms thereof.

Examples of portions of immunologically active immunoglobulin molecules include F(ab) and F(ab')$_2$ that can be generated by treating an antibody with an enzyme such as pepsin. The antibodies may be polyclonal (typically include different antibodies directed against different determinants or epitopes) or monoclonal antibodies (directed against a single determinant on the antigen). The antibody may also be recombinant, chimeric, humanized, synthetic or a combination of any of the above.

In one embodiment, the lectin is immobilized. Immobilization is usually achieved by attachment to a support. As used in the present invention, the term "support" refers to any solid material to which the components of the invention are physically bound, thus being immobilized. Solid supports suitable for their use in the present invention include but are not limited to silicone, glass, quartz, polyimide, acrylate, polymethylmethacrylate, ceramic, nitrocellulose, metals, amorphous silicon carbide, polystyrene as well as any other material suitable for micromanufacture or microlithography.

The lectin can be immobilized to the support by means of covalent bonds or by means of non-covalent bonds such as hydrogen bridges, hydrophobic interactions or ionic bonds. A general review of suitable microarrays and of supports has been described in Shalon et al. (Genome Research 6: 639-645 (1996)), LeGendre (BioTechniques 9: 788-805 (1990)), U.S. Pat. Nos. 6,197,599 and 6,140,045. Alternatively, it is possible to use supports activated by means of epoxy groups, vinyl sulfonic groups, active ester groups, aldehyde groups, carboxyl groups, amino groups, thiol groups, isothiocyanate groups and the like. In the event that the support is activated by means of epoxy groups, these groups include 3-glycidoxypropyltrimethoxysilane (GTMS), 2-(3,4-epoxycyclohexyl)ethyltrimethoxysilane, 3-glycidoxypropylmethyldiethoxysilane, 3-glycidoxypropyltriethoxysilane and the like.

In one embodiment, component of the kits according to the invention contain a label. In principle, the invention contemplates the use of any label provided that covalent conjugation to component b of the kit is possible and that it allows the subsequent detection of said component. In a preferred embodiment, the label can be detected by a change in at least one of its chemical, electrical or magnetic properties Thus, the invention contemplates the possibility of modifying the proteins with a radioisotope of the type of $^3$H, $^{11}$C, $^{14}$C, $^{18}$F, $^{32}$P, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{177}$Lu, $^{211}$At or $^{213}$B. The labeling with radioisotopes is typically carried out by means of using chelating ligands which are capable of complexing metal ions such as DOTA, DOTP, DOTMA, DTPA and TETA (Macrocyclics, Dallas, Tex.).

Nevertheless, in a preferred embodiment, component a is labeled with a fluorescent group. Suitable fluorescent compounds for use in the present invention include but are not limited to ethidium bromide, SYBR Green, fluorescein isothiocyanate (FITC), tetramethyl rhodamine isothiol (TRIT), 5-carboxyfluorescein, 6-carboxyfluorescein, fluorescein, HEX (6-carboxy-2',4,4',5',7,7'-hexachlorofluorescein), Oregon Green 488, Oregon Green 500, Oregon Green 514, Joe (6-carboxy-4',5'-dichloro-2',7'-dimethoxyfluorescein), 5-carboxy-2',4',5',7'-tetrachlorofluorescein, 5-carboxyrhodamine, rhodamine, tetramethylrhodamine (Tamra), Rox (carboxy-X-rhodamine), R6G (rhodamine 6G), phthalocyanines, azomethines, cyanines (Cy2, Cy3 and Cy5), Texas Red, Princeton Red, BODIPY FL-Br2, BODIPY 530/550, BODIPY TMR, BODIPY 558/568, BODIPY 564/570, BODIPY 576/589, BODIPY 581/591, BODIPY TR, BODIPY 630/650, BODIPY 650/665, DABCYL, Eosin, Erythrosine, ethidium bromide, green fluorescent protein (GFP) and the analogs thereof, inorganic fluorescent labels based on semiconductor nanocrystals (Quantum dot), fluorescent labels based on lanthanides such as Eu$^{3+}$ and Sm$^{3+}$ and the like.

In yet another embodiment, the kit contains a third component (component c) which is capable of specifically binding to component b. In this case, detection of the Apo J captured in the support by the lectin is not carried out by directly detecting component b, but rather by detecting component c once it is bound to component a.

Any molecule can be used as third component of the kit provided that it is capable of specifically binding to component b. In one embodiment, component b is modified with a first member of a binding pair and component c is modified with a second member of a binding pair.

The term "binding pair" refers to a couple of molecules (referred to first and second member of the binding pair) having the capacity to bind specifically by means of any type of intermolecular interaction including but not limited to biochemical, physiological and/or chemical interactions. The binding pair includes any type of interaction of immune type such as antigen/antibody, antigen/antibody fragment, hapten/anti-hapten as well as interactions of non-immune type such as avidin/biotin, avidin/biotinylated molecules, folic acid/folate-binding protein, hormone/hormone receptor, lectin/carbohydrate, lectin/molecule modified with carbohydrates, enzyme/enzyme substrate, enzyme/enzyme inhibitor, protein A/antibody, protein G/antibody, complementary nucleic acids (including sequences of DNA, RNA and peptide nucleic acids (PNA)), polynucleotide/polynucleotide-binding protein and the like.

It will be understood that the term "first" and "second" member of a binding pair is relative and that each of the previous members can be seen as the first or second member of the binding pair.

In an even more preferred embodiment wherein component b of the kit according to the invention is an antibody, in which case the third component is an antibody which is capable of specifically binding to said component b. In this case, the second antibody contains a label. Suitable labels for the third component of the kit are the same as those mentioned above for component b of the kit. The label of the third component of the kit can be a fluorescent group, a group luminescent or an enzyme. If the detectable compound is an enzyme, then this enzyme must be capable of generating a detectable signal, for example, after adding an activator, substrate, amplifying agent and the like. The enzymes which are suitable as detectable tags for the present invention and the corresponding substrates include:

Alkaline phosphatase:
    Chromogenic substrates: substrates based on p-nitrophenyl phosphate (p-NPP), 5-bromo-4-chloro-3-indolyl phosphate/nitroblue tetrazolium (BCIP/NBT), Fast-Red/naphthol phosphate-AS-TS
    Fluorogenic substrates: 4-methylumbelliferyl phosphate (4-MUP), 2-(5'-chloro-2'-phosphoryloxyphenyl)-6-chloro-4-(3H)-quinazolinone (CPPCQ), 3,6-fluorescein diphosphate (3,6-FDP), diazonium salts of Fast Blue BB, Fast Red TR, or Fast Red Violet LB.

Peroxidases:
    Chromogenic substrates based on 2,2-azinobis(3-ethylbenzothiazoline-6-sulfonic) acid (ABTS), o-phenylenediamine (OPT), 3,3',5,5'-tetramethylbenzidine (TMB), o-dianisidine, 5-aminosalicylic acid, 3-dimethylaminobenzoic acid (DMAB) and 3-methyl-2-benzothiazolinehydrazone (MBTH), 3-amino-9-ethylcarbazole (AEC) and 3,3'-diaminobenzidine (DAB) tetrahydrochloride.
    Fluorogenic substrates: 4-hydroxy-3-methoxyphenylacetic acid, reduced phenoxazines, reduced benzothiazines, including Amplex® Red reagent, Amplex UltraRed reagent and reduced dihydroxanthenes.

Glycosidases:
    Chromogenic substrates: o-nitrophenyl-β-D-galactoside (O—NPG), p-nitrophenyl-β-D-galactoside and 4-methylumbelliphenyl-β-D-galactoside (MUG) for β-D-galactosidase.
    Fluorogenic substrates: resorufin β-D-galactopyranoside, fluorescein digalactoside (FDG), fluorescein diglucuronide, 4-methylumbelliphenyl-β-D-galactopyranoside, carboxyumbelliferyl-β-D-galactopyranoside and fluorinated coumarin β-D-galactopyranosides.

Oxidoreductases (luciferase):
    Luminescent substrates: luciferin.

In the case of an enzymatic label, the kit may contain as an additional component one or more substrates of the enzyme.

In an even more preferred embodiment, the detectable compound which is bound to the second member of the binding pair is a fluorescent compound. As used in the present invention, the term "fluorescent compound" refers to all those compounds which absorb light at a determined wavelength or wavelength range and emit light at a different wavelength or wavelength range. Fluorescent compounds suitable for their use in the present invention include but are not limited to ethidium bromide, SYBR Green, fluorescein isothiocyanate (FITC), tetramethyl rhodamine isothiol (TRIT), 5-carboxyfluorescein, 6-carboxyfluorescein, fluorescein, HEX (6-carboxy-2',4,4',5',7,7'-hexachlorofluorescein), Oregon Green 488, Oregon Green 500, Oregon Green 514, Joe (6-carboxy-4',5'-dichloro-2',7'-dimethoxyfluorescein), 5-carboxy-2',4',5',7'-tetrachlorofluorescein, 5-carboxyrhodamine, rhodamine, tetramethylrhodamine (Tamra), Rox (carboxy-X-rhodamine), R6G (rhodamine 6G), phthalocyanines, azomethines, cyanines (Cy2, Cy3 and Cy5), Texas Red, Princeton Red, BODIPY FL-Br2, BODIPY 530/550, BODIPY TMR, BODIPY 558/568, BODIPY 564/570, BODIPY 576/589, BODIPY 581/591, BODIPY TR, BODIPY 630/650, BODIPY 650/665, DABCYL, Eosin, Erythrosine, ethidium bromide, green fluorescent protein (GFP) and the analogs thereof, inorganic fluorescent labels based on semiconductor nanocrystals (Quantum dot), fluorescent labels based on lanthanides such as Eu3+ and Sm3+ and the like.

Optionally, in a further embodiment, the kit further comprises a blank as a background control and/or a standard curve containing different concentrations of glycosylated Apo J.

In further aspects, the invention relates to the use of the kit according to the invention and as defined above in a method for the diagnosis of ischemia or ischemic tissue damage in a subject, for predicting the progression of ischemia in a patient having suffered an ischemic event, for determining the prognosis of a patient having suffered an ischemic event or for determining the risk that a patient suffering from stable coronary disease suffers a recurrent ischemic event.

Method for the Determination of Glycosylated Apo J in a Sample

In another aspect, the invention relates to a method for the determination of glycosylated Apo J in a sample comprising the steps of:
(i) Contacting the sample with a lectin which specifically binds to a glycan residue present in glycosylated Apo J under conditions adequate for the formation of a complex between the glycosylated Apo J in the sample and the lectin and
(ii) Detecting the amount of complex containing the lectin and the glycosylated Apo J to N-acetylglucosamine (GlcNAc).

The terms "glycosylated Apo J", "sample" and "lectin which specifically binds to a glycan residue present in glycosylated Apo J" have been described in detail in the context of the diagnostic and prognostic method of the invention as well as in the context of a kit according to the invention and are equally applicable to the method for the determination of glycosylated Apo J according to the invention.

In step (i), the method for the determination of glycosylated Apo J comprises contacting the sample with a lectin which specifically binds to a glycan residue present in glycosylated Apo J under conditions adequate for the formation of a complex between the glycosylated Apo J in the sample and the lectin.

Suitable conditions for the formation of said complex may be determined by the skilled person and include appropriate temperature, time of incubation, and pH. In a particular embodiment, the temperature ranges from 4 to 40° C., in particular from 10 to 35° C., more particularly from 15 to 30° C., preferably from 20 to 25° C. (room temperature). In a particular embodiment, the pH ranges from pH 2 to pH 10, preferably from pH 4 to pH 10. In a particular embodiment, step (i) is allowed to proceed for at least 1 minute, preferably for at least 5 minutes, more preferably for at least 30 minutes, even more preferably for at least 60 minutes.

In some embodiment, the sample is diluted prior to the contacting with the lectin. Suitable dilutions of a sample range from 1:10 to 1:100000, preferably from 1:100 to 1:1000, more preferably the dilution of the plasma sample is 1:200 or 1:1500

In one embodiment, the lectin used in step (i) is a lectin which specifically binds to N-acetylglucosamine or a lectin which specifically binds to N-acetylglucosamine and sialic acid. In a more preferred embodiment, the lectin which specifically binds to N-acetylglucosamine is the lectin from *Datura stramonium* or wherein the lectin which specifically binds to N-acetylglucosamine and sialic acid or to sialic acid is the lectin from *Triticum vulgaris*.

In yet another embodiment, the lectin which specifically binds to a glycan residue is immobilized. Suitable supports are the same as those described in the kit of the invention.

Once step (i) has proceeded for sufficient time to allow the formation of a complex between the lectin and the glycosylated Apo J present in the sample, step (ii) is carried out. In step (ii), the method for the determination of glycosylated Apo J comprises detecting the amount of complex containing the lectin and the glycosylated Apo J.

In one embodiment, the complexes obtained in step (i) are washed prior to starting step (ii) in order to remove any Apo J which might have been attached to the support via non-specific binding. The washing after step (i) is carried out using a washing solution. In a particular embodiment, the washing solution contains one or more salts. Preferably, the salt contained by the washing solution is NaCl, comprised by a Tris buffer (TBS) or by a phosphate buffer (PBS). Additionally or alternatively, the washing solution contains at least one detergent. Preferably, the detergent is selected from the group consisting of polysorbate 20 (Tween 20) and Triton X-100

The detection of the amount of complex containing the lectin and the glycosylated Apo J is usually carried out using a reagent that specifically binds to the Apo J polypeptide. In a preferred embodiment, the reagent that specifically binds to the Apo J polypeptide is an antibody or a fragment thereof containing its antigen-binding region.

Suitable antibodies for use in step (ii) of the method for detecting glycosylated Apo J have been defined in the context of the kit according to the invention and are equally applicable herein. In one embodiment, the antibody is coupled to a detectable label. Suitable labels for the anti-Apo J antibody are defined above in the context of the kit according to the invention. In a preferred embodiment, the label can be detected by means of a change in at least one of its chemical, electrical or magnetic properties.

In another embodiment, the detection of the amount of complex containing the lectin and the glycosylated Apo J is carried out using a reagent which is capable of specifically binding to the reagent that specifically binds to the Apo J polypeptide. In another embodiment, the third reagent which is capable of specifically binding to the reagent that specifically binds to the Apo J polypeptide is an antibody or a fragment thereof containing its antigen-binding region, in which case the complex is detected by detecting the antibody which has bound to the reagent that specifically binds to the Apo J. This is done by using an antibody that contains a detectable label. Suitable labels for use in the antibody are defined above in the context of the kit according to the invention. The label can be a fluorescent label or an enzymatic label.

The present invention will be illustrated by the following examples which do not intend to limit the scope of the instant invention.

EXAMPLES

Example 1

Figure 1:
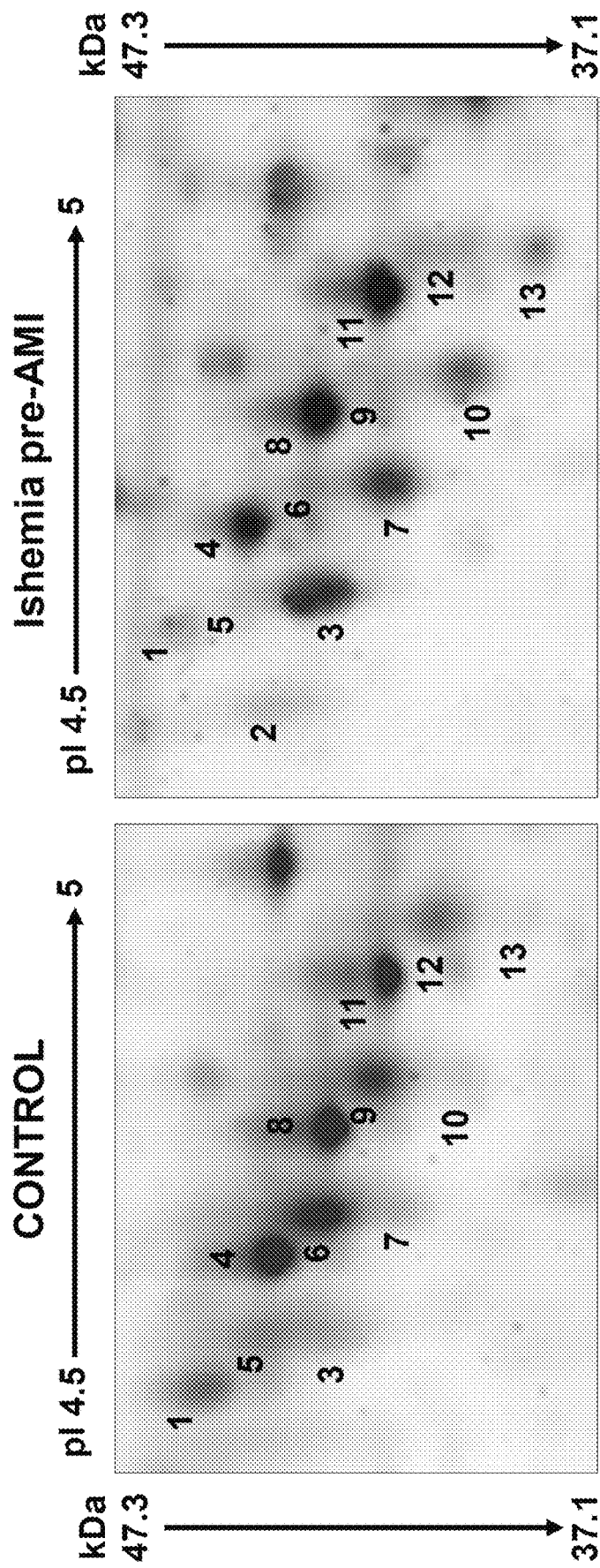
FIG. 1. Apo J 2-DE Profile.

Diagnostic Value of Apo J-GlcNAc+Neu5Ac+Apo J-GlcNAc and Apo J-GlcNAc in Cardiac Ischemia The Apo J proteomic profile in cardiac ischemia patients has been previously characterised using bi-dimensional electrophoresis (2-DE) followed by mass spectrometry identification (Cubedo, J., et al., 2011, Journal of proteome research 10: 211-220). In that study, it was shown that specific Apo J forms were either increased (Apo J-29) or decreased (Apo J-15) within the first six hours after the onset of the event (FIG. 1). By applying these criteria, it was proposed that specific Apo J forms (Apo J-15 and Apo J-29) were markers of tissue damage as that induced by an acute myocardial infarction (AMI). In the same study, it was also analysed if the changes detected in Apo J-15 and Apo J-29 could be due to changes in the glycosylation profile of Apo J. Specifically, serum glycoproteins were isolated with a mixture of Concavalin A and *Triticum vulgaris* lectins (that binds proteins with α-mannose, α-glucose, (GlcNAc)$_2$ and Neu5Ac residues). The isolated proteins were analyzed by 2-DE analysis followed by mass spectrometry identification. In this analysis (FIG. 2), it was found that only spots 1, 2, 4, 5, 8 and 11 contained α-mannose, α-glucose, (GlcNAc)$_2$ and Neu5Ac residues, whereas spots 3, 6, 7, 9, 10, 12 and 13 did not have those residues. The intensity of glycosylated Apo J spots with α-mannose, α-glucose, (GlcNAc)$_2$ and Neu5Ac residues was lower in ischemia pre-AMI patients than in controls. This decrease was more evident in forms 4 and 8. There was a 25% decrease in total α-mannose, α-glucose, (GlcNAc)$_2$ and Neu5Ac glycosylated Apo J intensity in the early phase of ischemia. On the contrary, Apo J forms without those residues (3, 6, 7, 10, 12 and 13) were increased in the early phase of ischemia.

However, due to the multiple specificity of the lectins used in the assays described above, these assays were unable to discriminate which of the different glycosylated forms of Apo J (forms containing α-mannose, forms containing α-glucose, forms containing (GlcNAc)$_2$ and/or forms containing Neu5Ac residues) were actually the biomarkers which were associated with ischemic damage. In addition, by using the *Artocarpus integrifolia* lectin, which binds proteins with α-galactose and GalNAc residues, which are found only in 0-glycans, it was found (FIG. 3), that only spots 1, 3, 4, 6, 7, 8, 9, 11 and 12 contained α-galactose and GalNAc residues, whereas spots 2, 5, 10 and 13 did not have those residues. Therefore, the previously reported decrease in spots 1, 2, 4, 5, 8 and 11 was not only indicative of a decrease in forms containing α-mannose, α-glucose, (GlcNAc)$_2$ and Neu5Ac residues because some of those spots also contain O-glycosylated residues and more specifically α-galactose and GalNAc residues.

In order to discriminate the presence of different types of residues in Apo J, a distinct methodology has been used. This methodology (hereinafter known as immunoaffinity enzymatic-glycosylation assay or EGA) allows the specific detection and quantification of different glycosylated Apo J forms. This EGA is based on: 1) a first step in which proteins are immobilized by their binding to a specific glycosylation residue (Table 1), 2) a second step, in which Apo J is detected with a monoclonal or polyclonal antibody against Apo J protein sequence, and 3) a final step in which the amount of the specific immobilized glycosylated Apo J form is further detected and quantified by a reporter system or molecule. This reporter system could consist in: a) a colorimetric system such as a secondary antibody together with a reporter system such as biotin-streptavidin-HRP; or b) a physicochemical change in the system (i.e. chemical, electrical or magnetic change).

TABLE 1

Glycans and carbohydrate structures present in Apo J and specific lectin-based methodological approach used to detect it.

| Methodological approach | Lectin type | Glycan/Carbohydrate structure |
| --- | --- | --- |
| Lectin-based glycoprotein isolation + 2DE analysis and MS Apo J identification | Concavalin A + *Triticum vulargis* | α-mannose + α-glucose + (GlcNAc)$_2$ + Neu5Ac |
|  | *Artocarpus integrifolia* | α-galactose + GalNAc |
| Lectin-based Enzymatic Glycosylation Assay -EGA- Apo J glycan type validation | *Triticum vulgaris* *Sambucus nigra* *Ulex europaeus* *Glycine max* *Datura stramonium* | GalNAc + Neu5Ac αNeu5Ac(2→6)gal + GalNAc α-L-fucose GalNac (GlcNAc)$_2$ |

Using this methodology with different lectins, it has been found that glycosylated Apo J can have the following glycan residues: a) (GlcNAc)$_2$+Neu5Ac; b) αNeu5Ac(2→6)gal+GalNAc; c) α-L-fucose; d) GalNAc alone; and e) (GlcNAc)$_2$ alone (FIG. 4).

The EGA was then applied to specifically measure Apo J with (GlcNAc)$_2$+Neu5Ac residues (Apo J-GlcNAc+Neu5Ac+Apo J-GlcNAc) in plasma samples of 38 ischemia pre-AMI patients and 144 healthy controls. It was found that ischemia pre-AMI patients showed a 45% decrease in Apo J-GlcNAc+Neu5Ac+Apo J-GlcNAc levels in the early phase of ischemia when compared to controls (Ischemia pre-AMI: 264±18 vs. C: 473±6 µg/mL; P<0.0001; FIG. 5A). Samples of ischemia pre-AMI patients were taken at the moment of admission (t=0) within the first 6 hours after the onset of chest pain and before the raising of necrosis markers (T-troponin and CK). At this time point patients had not received any treatment because of the event onset. The C-statistics analysis revealed that the measurement of Apo J-GlcNAc+Neu5Ac+Apo J-GlcNAc levels with EGA showed a high discriminating value for the presence of myocardial ischemia with an area under the curve (AUC) of 0.934 (P<0.0001) and a cut-off value of 332 µg/mL with 97% of sensitivity and 71% of specificity (FIG. 5B and Table 2). Therefore, the measurement of Apo J-GlcNAc+Neu5Ac+Apo J-GlcNAc levels could be used as a biomarker for the diagnosis of ischemia.

We further analyzed Apo J-GlcNAc+Neu5Ac+Apo J-GlcNAc levels in 212 STEMI-patients with the EGA methodology. Samples were taken at admission in STEMI-patients (including de novo and secondary events) with different times of evolution of the ischemic pain (1 h-60 h) including patients with positive T-troponin detection at admission (group of patients with necrosis). STEMI-patients showed a 15% reduction in Apo J-GlcNAc+Neu5Ac+Apo J-GlcNAc plasma levels at admission when compared with the control group (STEMI: 402±8 vs. C: 473±6 µg/mL; P<0.0001; FIG. 6A). C-statistics analysis revealed that the measurement of Apo J-GlcNAc+Neu5Ac+Apo J-GlcNAc levels with EGA showed a discriminating ability for the presence of myocardial ischemia with an area under the curve (AUC) of 0.713 (P<0.0001) and a cut-off value of 409 µg/mL with 80% of sensitivity and 53% of specificity (FIG. 6B). When the EGA was then applied to specifically measure Apo J with (GlcNAc)$_2$ residues (Apo J-GlcNAc) with the lectin *Datura stramonium* in 340 STEMI-patients and in 139 healthy controls a 35% decrease in Apo J-GlcNAc plasma levels was found in STEMI-patients at the moment of admission (STEMI: 328±7 vs. C: 506±12 µg/mL; P<0.0001; FIG. 6C). C-statistics analysis revealed that the measurement of Apo J-GlcNAc levels showed a higher discriminating ability for the presence of myocardial ischemia with an area under the curve (AUC) of 0.830 (P<0.0001) and a cut-off value of 393 µg/mL with 81% of sensitivity and 72% of specificity (FIG. 6D).

to the moment of admission (t=72 h: 331±10 vs. t=0: 402±8 µg/mL; P<0.0001; FIG. 7B). When only Apo J-GlcNAc levels were analyzed there was also a significant and inverse correlation with ischemia time (R=−0.113 P=0.048; FIG. 7C). These results highlight that Apo J-GlcNAc+Neu5Ac+Apo J-GlcNAc and Apo J-GlcNAc are novel biomarkers of ischemia progression.

Furthermore, STEMI-patients with a final TIMI-flow grade of 0 or 1, which is associated to a worse prognosis due to an increased risk of in-hospital and 6-months mortality, showed significantly lower Apo J-GlcNAc+Neu5Ac+Apo J-GlcNAc plasma levels when compared to those STEMI-patients with a final TIMI flow of ≥2 (FIG. 8A). In addition, those patients who suffered a cardiogenic shock, which is associated with a poorer prognosis after suffering a STEMI, showed 12% lower Apo J-GlcNAc+Neu5Ac+Apo J-GlcNAc plasma levels at admission when compared to those who did not had a cardiogenic shock (FIG. 8B).

In addition, there was an inverse and significant correlation between Apo J-GlcNAc+Neu5Ac+Apo J-GlcNAc levels and the GRACE Risk score, which is related to mortality (R=−0.257 P=0.0002; FIG. 9A). Moreover, looking at the change in Apo J-GlcNAc+Neu5Ac levels in the follow-up of those 82 STEMI-patients we observed that those patients whose Apo J-GlcNAc+Neu5Ac+Apo J-GlcNAc levels were even lower 3 days after the event than in the moment of admission showed higher GRACE Risk Score values (P=0.002; FIG. 9B). Similarly, Apo J-GlcNAc levels were also inversely and significantly correlated with the GRACE Risk score (R=−0.184 P=0.0006; FIG. 9C). All these results point out to an unexpected role of Apo J-GlcNAc+Neu5Ac+Apo J-GlcNAc and Apo J-GlcNAc as risk stratification markers in the context of ischemic events.

Moreover, Kaplan-Meier survival analysis revealed that those patients with Apo J-GlcNAc+Neu5Ac+Apo J-GlcNAc levels below the median value of the STEMI group at admission showed a significant difference in the appearance of recurrent ischemic events and in the mortality rate after 6

TABLE 2

Cut-off values and associated sensitivity and specificity applicable to the method for diagnosis of myocardial damage, to the method for the diagnosis of cerebral ischemia, to the method for the prognosis of mortality and of recurrent events and for the method for the risk stratification in patients suffering stable CAD together with the corresponding sensitivity and specificity values.

|  | Glycosylated Apo J form | Cut-off value | Sensitivity | Specificity |
| --- | --- | --- | --- | --- |
| Diagnosis: myocardial ischemia pre-AMI | Apo J-GlcNAc + Neu5Ac + Apo J-GlcNAc | <332 µg/mL | 97% | 71% |
| Diagnosis: myocardial ischemia STEMI | Apo J-GlcNAc + Neu5Ac + Apo J-GlcNAc | <409 µg/mL | 80% | 53% |
|  | Apo J-GlcNAc | <393 µg/mL | 81% | 72% |
| Diagnosis: cerebral ischemia | Apo J-GlcNAc + Neu5Ac + Apo J-GlcNAc | <424 µg/mL | 66% | 51% |
| Prognosis: mortality and recurrent events | Apo J-GlcNAc + Neu5Ac + Apo J-GlcNAc | <398 µg/mL | 55% | 65% |
|  | Apo J-GlcNAc | <287 µg/mL | 58% | 51% |
| Prognosis: mortality | Apo J-GlcNAc | <273 µg/mL | 64% | 50% |
| Risk stratification: recurrent events in stable CAD | Apo J-GlcNAc + Neu5Ac + Apo J-GlcNAc | <485 µg/mL | 94% | 64% |

Example 2

Prognostic Value of Apo J-GlcNAc+Neu5Ac+Apo J-GlcNAc and of Apo J-GlcNAc

In a second phase we evaluated if the specific quantification glycosylated Apo J forms could have a prognostic value. Apo J-GlcNAc+Neu5Ac+Apo J-GlcNAc levels were significantly and inversely correlated with ischemia time (defined as the elapsed time between the onset of symptoms and admission; R=−0.259 P=0.0003; FIG. 7A). Moreover, the measurement of Apo J-GlcNAc+Neu5Ac+Apo J-GlcNAc levels in 82 STEMI-patients 3 days after the admission revealed a progressive decrease when compared months of follow-up (P=0.008; FIG. 10A). This effect was not seen when the same analysis was performed with T-troponin (P=0.363; FIG. 10B). Apo J-GlcNAc levels also have a prognostic value as Kaplan-Meier survival analysis revealed that those STEMI patients with Apo J-GlcNAc levels within the lowest quartile at admission (<236.8 µg/mL) showed a significant decrease in the survival rate at 6-months of follow-up (P=0.015; FIG. 10C). A significant difference was also observed when both, the appearance of recurrent ischemic events and mortality after 6 months of follow-up were taken as endpoints in the Kaplan-Meier analysis between STEMI patients with Apo J-GlcNAc levels within the lowest quartile at admission (<236.8 µg/mL) and those showing higher Apo J-GlcNAc values at admission (P=0.031; FIG. 10D). Thus our results point out to a role of Apo J-GlcNAc+Neu5Ac+Apo J-GlcNAc and Apo J-GlcNAc plasma levels as prognostic markers after ischemia presentation.

Example 3

Predictive Value Apo J-GlcNAc+Neu5Ac+Apo J-GlcNAc for the Presentation of Recurrent Ischemic Events (Either Cardiac or Cerebral) in the Context of Stable Coronary Artery Disease (CAD).

The present study has shown another unexpected property of Apo J-GlcNAc+Neu5Ac+Apo J-GlcNAc measurement, a predictive value for the presentation of recurrent ischemic events (either cardiac or cerebral) in the context of stable coronary artery disease (CAD). We have analyzed Apo J-GlcNAc+Neu5Ac+Apo J-GlcNAc levels in a group of chronic CAD patients (N=34) that had suffered an acute coronary syndrome (ACS) a mean of 0.6±0.04 years before sample collection and were followed-up for 2.3±0.3 years afterwards (FIG. 11A). Plasma samples were obtained from two groups of patients: those who suffered an acute ischemic event (any acute coronary syndrome (ACS), stroke or transient ischemic event (TIA)) at follow-up (N=16) and those who did not had acute ischemic events (N=18) during the follow-up period. There were no significant differences in age, incidence of diabetes and hypertension, and cholesterol parameters between both groups. None of the included patients were smokers and all of them were under antiplatelet therapy at the moment of sample collection. Patients who suffered a recurrent event showed 28% lower Apo J-GlcNAc+Neu5Ac+Apo J-GlcNAc levels before suffering the event than those who did not had any event at follow-up (FIG. 11B). Indeed, the receiver operating curve (ROC) showed a predictive value of Apo J-GlcNAc+Neu5Ac+Apo J-GlcNAc levels for the presentation of recurrent ischemic event in stable CAD patients (FIG. 11C). Specifically, in the present study, Apo J-GlcNAc+Neu5Ac+Apo J-GlcNAc levels below 485 µg/mL were able to predict the presentation of a recurrent ischemic event with 94% sensitivity and 64% specificity in stable CAD patients (Table 2). Thus Apo J-GlcNAc+Neu5Ac+Apo J-GlcNAc shows an additional value as a marker of the "silent" ischemic process preceding the presentation of a recurrent acute ischemic event in patients with stable CAD.

Example 4

Role of Apo J-GlcNAc+Neu5Ac+Apo J-GlcNAc as Biomarker in Cerebral Ischemia

Additionally, the measurement of Apo J-GlcNAc+Neu5Ac+Apo J-GlcNAc levels in 174 stroke patients revealed a 8% decrease when compared to 164 healthy controls (Stroke: 418±7 vs. C: 453±7 µg/mL; P=0.0008; FIG. 12), highlighting that Apo J-GlcNAc+Neu5Ac+Apo J-GlcNAc is also a biomarker of cerebral ischemia.

The invention claimed is:
1. A method for the diagnosis of ischemia or ischemic tissue damage in a subject comprising the steps of:
(a) determining in a sample of said subject the levels of glycosylated Apo J containing N-acetylglucosamine (GlcNAc) residues or the levels of glycosylated Apo J containing N-acetylglucosamine (GlcNAc) and sialic acid residues,
(b) comparing the levels of Apo J containing N-acetylglucosamine (GlcNAc) residues with respect to a reference value or the levels of Apo J containing N-acetylglucosamine (GlcNAc) and sialic acid residues with respect to a reference value, and
(c) diagnosing ischemia or ischemic tissue damage in the subject if the sample shows decreased levels of Apo J containing N-acetylglucosamine (GlcNAc) residues with respect to the reference value or decreased levels of Apo J containing N-acetylglucosamine (GlcNAc) and sialic acid residues with respect to the reference value, wherein the determination of step (a) is performed by a method comprising the steps of:
(i) Contacting the sample with a *Triticum vulgaris* (*T. vulgaris*) lectin which specifically binds to a glycan residue present in glycosylated Apo J under conditions adequate for the formation of a complex between the glycosylated Apo J in the sample and the lectin wherein the lectin has been immobilized on a support prior to contacting the sample with the lectin; and
(ii) Detecting the amount of complex containing the lectin and the glycosylated Apo J using an antibody capable of specifically binding to the Apo J polypeptide or a fragment thereof containing its antigen-binding region.

2. A method for predicting the progression of ischemia in a patient having suffered an ischemic event or for determining the prognosis of a patient having suffered an ischemic event, comprising the steps of:
(a) determining in a sample of said patient the levels of glycosylated Apo J,
(b) comparing the levels of glycosylated Apo J with a reference valued, and
(c) predicting that ischemia is progressing or a poor prognosis of the patient if the levels of glycosylated Apo J are decreased with respect to the reference value, wherein the determination in step (a) is performed using a method comprising the steps of:
(i) Contacting the sample with a *Triticum vulgaris* (*T. vulgaris*) lectin which specifically binds to a glycan residue present in glycosylated Apo J under conditions adequate for the formation of a complex between the glycosylated Apo J in the sample and the lectin wherein the lectin has been immobilized on a support prior to the contacting of the sample with the lectin; and
(ii) Detecting the amount of complex containing the lectin and the glycosylated Apo J using an antibody capable of specifically binding to the Apo J polypeptide or a fragment thereof containing its antigen-binding region.

3. A method for determining the risk that a patient suffering from stable coronary disease suffers a recurrent ischemic event comprising the steps of:
(a) determining in a sample of said patient the levels of glycosylated Apo J,
(b) comparing the levels of glycosylated Apo J with a reference value, and
(c) determining that the risk that the patient suffering from stable coronary disease suffers a recurrent ischemic event is increased if the levels of glycosylate Apo J are decreased with respect to a reference value, wherein the determination in step (a) is performed using a method comprising the steps of:
Contacting the sample with a *Triticum vulgaris* (*T. vulgaris*) lectin which specifically binds to a glycan residue present in glycosylated Apo J under conditions adequate for the formation of a complex between the glycosylated Apo J in the sample and the lectin wherein the lectin has been immobilized on a support prior to the contacting of the sample with the lectin; and (ii) Detecting the amount of complex containing the lectin and the glycosylated Apo J using an antibody capable of specifically binding to the Apo J polypeptide or a fragment thereof containing its antigen-binding region.

4. A method for the determination of glycosylated Apo J in a sample comprising the steps of:

(i) Contacting the sample with a *Triticum vulgaris* (*T. vulgaris*) lectin which specifically binds to a glycan residue present in glycosylated Apo J under conditions adequate for the formation of a complex between the glycosylated Apo J in the sample and the lectin, wherein the lectin has been immobilized on a support prior to the contacting of the sample with the lectin; and (ii) Detecting the amount of complex containing the lectin and the glycosylated Apo J using an antibody capable of specifically binding to the Apo J polypeptide or a fragment thereof containing its antigen-binding region.

5. The method according to claim 4 wherein the lectin used in step (i) is a lectin which specifically binds to N-acetylglucosamine or a lectin which specifically binds to N-acetylglucosamine and sialic acid.

6. The method of claim 4 wherein the antibody is coupled to a detectable label.

7. The method of claim 6 wherein the label can be detected by means of a change in at least one of its chemical, electrical or magnetic properties.

8. The method according to claim 1 wherein the ischemia is myocardial or cerebral ischemia.

9. The method of claim 8 wherein the myocardial ischemia is acute myocardial ischemia or microvascular angina.

10. The method of claim 1 wherein the cerebral ischemia is stroke.

11. The method of claim 1 wherein the patient is suspected to have suffered an ischemic event.

12. The method of claim 1 wherein the determination is carried out within the first 6 hours after the onset of the suspected ischemic event, before the raising of the levels of at least one necrotic marker or before the patient has received any treatment for the suspected ischemic event.

13. The method of claim 1 wherein levels of glycosylated Apo J containing N-acetylglucosamine (GlcNAc) and sialic acid residues correspond to the levels of Apo J capable of specifically binding to the *T. vulgaris lectin*.

14. The method of claim 1 wherein the sample is a biofluid.

15. The method of claim 14 wherein the biofluid is plasma or serum.

16. The method of claim 2 wherein the glycosylated Apo J is glycosylated Apo J containing N-acetylglucosamine (GlcNAc) residues or glycosylated Apo J containing N-acetylglucosamine (GlcNAc) and sialic acid residues.

17. The method according to claim 2 wherein the ischemic event is a myocardial ischemic event.

18. The method according to claim 17 wherein the myocardial ischemic event is a ST-elevation myocardial infarction.

19. The method according to claim 2 wherein the prognosis of the patient is determined as the risk of 6 months recurrence, the risk of in hospital mortality or the risk of 6-months mortality.

20. The method of claim 3 wherein the glycosylated Apo J is glycosylated Apo J containing N-acetylglucosamine (GlcNAc) residues or glycosylated Apo J containing N-acetylglucosamine (GlcNAc) and sialic acid residues.

21. The method of claim 2 wherein levels of glycosylated Apo J containing N-acetylglucosamine (GlcNAc) and sialic acid residues correspond to the levels of Apo J capable of specifically binding to the *T. vulgaris lectin*.

22. The method of claim 2 wherein the sample is a biofluid.

23. The method of claim 22 wherein the biofluid is plasma or serum.

24. The method of claim 3 wherein the patient suffering from stable coronary disease had suffered acute coronary syndrome prior to the stable coronary disease.

25. The method of claim 3 wherein the recurrent ischemic event is an acute coronary syndrome, a stroke or a transient ischemic event.

26. The method of claim 3 wherein levels of glycosylated Apo J containing N-acetylglucosamine (GlcNAc) and sialic acid residues correspond to the levels of Apo J capable of specifically binding to the *T. vulgaris lectin*.

27. The method of claim 3 wherein the sample is a biofluid.

28. The method of claim 27 wherein the biofluid is plasma or serum.

* * * * *